US010852293B2

(12) United States Patent
Otvos et al.

(10) Patent No.: US 10,852,293 B2
(45) Date of Patent: Dec. 1, 2020

(54) NMR MEASUREMENTS OF NMR BIOMARKER GLYCA

(71) Applicant: LipoScience, Inc., Raleigh, NC (US)

(72) Inventors: James D. Otvos, Apex, NC (US); Irina Y. Shalaurova, Cary, NC (US); Dennis W. Bennett, Shorewood, WI (US); Justyna E. Wolak-Dinsmore, Durham, NC (US)

(73) Assignee: LipoScience, Inc., Morrisville, NC (US)

(*) Notice: Subject to any disclaimer, the term of this patent is extended or adjusted under 35 U.S.C. 154(b) by 0 days.

(21) Appl. No.: 15/264,977

(22) Filed: Sep. 14, 2016

(65) Prior Publication Data
US 2017/0003269 A1 Jan. 5, 2017

Related U.S. Application Data

(63) Continuation of application No. 13/830,199, filed on Mar. 14, 2013, now Pat. No. 9,470,771.

(60) Provisional application No. 61/739,305, filed on Dec. 19, 2012, provisional application No. 61/711,471, filed on Oct. 9, 2012, provisional application No. 61/657,315, filed on Jun. 8, 2012.

(51) Int. Cl.
*G01N 33/49* (2006.01)
*G16H 50/30* (2018.01)
*A61B 5/00* (2006.01)
*G01R 33/46* (2006.01)
*G01N 24/08* (2006.01)
*G01R 33/465* (2006.01)
*A61B 5/055* (2006.01)

(52) U.S. Cl.
CPC .......... *G01N 33/49* (2013.01); *A61B 5/0044* (2013.01); *A61B 5/055* (2013.01); *A61B 5/7275* (2013.01); *G01N 24/08* (2013.01); *G01R 33/465* (2013.01); *G01R 33/4625* (2013.01); *G16H 50/30* (2018.01); *A61B 2576/023* (2013.01); *G01N 2333/47* (2013.01); *G01N 2333/4728* (2013.01); *G01N 2800/324* (2013.01); *G01N 2800/50* (2013.01)

(58) Field of Classification Search
CPC .. G16H 50/30; G01N 33/492; G01N 33/5091; G01N 2800/7095; G01N 2800/32; G01N 2800/323; G01N 2800/324; G01N 2800/325; G01N 2800/50; G01N 2333/4728; G01N 2333/47; G01N 24/08; G01N 24/087; G01R 33/465; G01R 33/4625; A61B 5/7275; A61B 5/055; A61B 5/0044; A61B 2576/023
See application file for complete search history.

(56) References Cited

U.S. PATENT DOCUMENTS

| | | |
|---|---|---|
| 4,529,710 A | 7/1985 | Spicer et al. |
| 4,933,844 A | 6/1990 | Otvos |
| 6,518,069 B1 | 2/2003 | Otvos et al. |
| 6,576,471 B2 | 6/2003 | Otvos |
| 6,617,167 B2 | 9/2003 | Otvos et al. |
| 7,243,030 B2 | 7/2007 | Reeve et al. |
| 7,491,543 B2 | 2/2009 | Barzilai |
| 7,790,465 B2 | 9/2010 | Otvos |
| 8,268,626 B2 | 9/2012 | Okazaki |
| 9,792,410 B2 | 10/2017 | Otvos et al. |
| 2003/0119194 A1 | 6/2003 | Otvos |
| 2004/0058386 A1 | 3/2004 | Wishart et al. |
| 2005/0074745 A1 | 4/2005 | Clayton et al. |
| 2005/0222504 A1 | 10/2005 | Otvos et al. |
| 2007/0264677 A1 | 11/2007 | Otvos |
| 2010/0100334 A1 | 4/2010 | Otvos |
| 2011/0034035 A1 | 2/2011 | Liang et al. |
| 2011/0034039 A1 | 2/2011 | Liang et al. |
| 2011/0111137 A1 | 5/2011 | Liang et al. |
| 2011/0136241 A1 | 6/2011 | Naylor |
| 2011/0165781 A1 | 7/2011 | Liang et al. |
| 2011/0189780 A1 | 8/2011 | Cerda et al. |
| 2011/0311650 A1 | 12/2011 | Wang et al. |
| 2012/0122981 A1 | 5/2012 | Hu et al. |
| 2015/0127267 A1 | 5/2015 | Otvos et al. |

(Continued)

FOREIGN PATENT DOCUMENTS

| | | |
|---|---|---|
| AU | 2013329308 | 2/2019 |
| CN | 104520699 | 4/2015 |
| CN | 104823055 | 8/2015 |

(Continued)

OTHER PUBLICATIONS

Alvarado, E. "Practical guide for quantitative 1D NMR integration." May 10, 2010. (Year: 2010).*

(Continued)

*Primary Examiner* — Christopher Adam Hixson

(74) *Attorney, Agent, or Firm* — Kilpatrick Townsend & Stockton LLP

(57) ABSTRACT

Biomarkers and/or risk assessments identify patients having an increased risk of certain clinical disease states including, for example, CHD, type 2 diabetes, dementia, or all-cause death (ACD) using NMR signal to measure a level of "GlycA" in arbitrary units or in defined units (e.g., µmol/L) that can be determined using a defined single peak region of proton NMR spectra. The GlycA measurement can be used as an inflammation biomarker for clinical disease states. The NMR signal for GlycA can include a fitting region of signal between about 2.080 ppm and 1.845 ppm of the proton NMR spectra.

12 Claims, 29 Drawing Sheets

(56) References Cited

U.S. PATENT DOCUMENTS

2015/0149095 A1     5/2015    Otvos et al.

FOREIGN PATENT DOCUMENTS

| | | |
|---|---|---|
| EP | 264815 | 4/1988 |
| JP | 2002543392 | 12/2002 |
| JP | 2006-317311 A | 11/2006 |
| JP | 2007-132752 A | 5/2007 |
| JP | 2009530627 | 8/2009 |
| JP | 2010534325 | 11/2010 |
| WO | WO 2006/057081 | 6/2006 |
| WO | 2007110357 | 10/2007 |
| WO | WO 2007/133593 | 11/2007 |
| WO | 2008137075 | 11/2008 |
| WO | 2010114897 | 10/2010 |
| WO | 2011/143779 A1 | 11/2011 |
| WO | 2013185014 | 12/2013 |

OTHER PUBLICATIONS

Bell, J. D. et al. "Assignment of resonances for 'acute-phase' glycoproteins in high resolution proton NMR spectra of human blood plasma." FEBS Journal (1987) 215 311-315. (Year: 1987).*

Danesh, John et al. "Low grade inflammation and coronary heart disease: prospective study and updated meta-analyses." BMJ (2000) 321 199-204. (Year: 2000).*

Liu, Maili et al. "Use of H-NMR-determined diffusion coefficients to characterize lipoprotein fractions in human blood plasma." Magnetic Resonance in Chemistry (2002) 40 s83-s88. (Year: 2002).*

AU 2013272014, "First Examiner Report", dated Sep. 27, 2016, 5 pages.

CN 201380041876.4, "Office Action", dated Nov. 2, 2016, 11 pages.

CN 201380041876.4, "Office Action", dated Mar. 13, 2017, 8 pages.

CN 201380064302.9, "Office Action", dated Mar. 22, 2017, 11 pages.

CN 201380064302.9, "Office Action", dated Sep. 19, 2016, 11 pages.

Hiltunen et al., "A lineshape fitting model for 1H NMR spectra of human blood plasma", Magn Reson Med., vol. 21, No. 2, Jan. 31, 1991, pp. 222-232.

JP 2015-516071, "Office Action", dated Nov. 15, 2016, 5 pages.

JP 2015-536865, "Office Action", dated May 23, 2017, 7 pages.

Psychogios et al., "The Human Serum Metabolome", PLoS One, Feb. 16, 2011, pp. 1-23.

Wei et al., "Toxicological effects of cinnabar in rats by NMR-based metabolic profiling of urine and serum", Toxicology and Applied Pharmacology, vol. 227, No. 3, Dec. 13, 2007, pp. 417-429.

Wishart et al., "The human cerebrospinal fluid metabolome", J Chromatogr B Analyt Technol Biomed Life Sci., vol. 871, No. 2, Aug. 5, 2008, pp. 164-173.

Akinkuolie et al. "A Novel Protein Glycan Biomarker and Future Cardiovascular Disease Events", J Am Heart Assoc. 2014, vol. 3, pp. 1-12.

Bell et al. "Assignment of resonances for acute-phase glycoproteins in high resolution proton NMR spetra of human blood plasma", FEBS Letters, vol. 215, No. 2, pp. 311-315, 1987.

Chang et al., "NMR Analysis on Gly", Journal of Anhui Agricultural Sciences, vol. 38, No. 19, Dec. 31, 2010, pp. 9937-9938.

Chung et al. "GiycA, A Novel Marker of Inflammation, Is Elevated in Systemic Lupus Erythematosus", Lupus, 2016, vol. 25, pp. 296-300.

European Patent Office, Supplementary European Search Report, European Application No. 13800239, dated Mar. 15, 2016, 8 pages.

Fogelman A. "When Good Cholesterol Goes Bad", Nature Medicine, vol. 10, No. 9, Sep. 2004, 902-903.

Gates et al., Glycoprotein Analysis Manual, Overview, 151 edition, 2004, Sigma Aldrich, https://www.siamaaldrich.com/ima/assets/15402/Givcoorotein Web PDF linked.odf.

International Search Report and Written Opinion for corresponding PCT Application No. PCT/US2013/043343, dated Sep. 25, 2013.

Jey Arajah et al. "Lipoprotein Particle Analysis by Nuclear Magnetic Resonance Spectroscopy", Clin Lab Med, 2006, vol. 26, pp. 847-870.

Liu et al., "Application of HNMR Technology in Amino Acid Analysis and ATM Degradation Product Detection", Medical Journal of National Defending Forces in Southwest China, vol. 12, No. 3, Dec. 31, 2002, pp. 247-248.

Muhlestein et al., "GiycA and GlycB, Novel NMR Biomarkers of Inflammation, Strongly Predict Future Cardiovascular Events, but Not the Presence of Coronary Artery Disease (CAD), among Patients Undergoing Coronary Angiography: The intermountain Heart Collaborative Study", Poster Contributions, JACC Apr. 1, 2014, vol. 63, Issue 12, p. 1.

Ormseth et al., "Utility of a Novel Inflammatory Marker, GlycA, for Assessment of Rheumatoid Arthritis Disease Activity and Coronary Atherosclerosis", Arthritis Research & Therapy, 2015, vol. 17, No. 117, pp. 1-8.

Otvos et al. "Quantification of Plasma Lipoproteins by Proton Nuclear Magnetic resonance Spectroscopy", Clin Chem, vol. 37, pp. 377-386, 1991.

Otvos et al., "GiycA: A Composite Nuclear Magnetic Resonance Biomarker of Systemic Inflammation", Clin Chem, vol. 61, No. 5, 2015, pp. 714-723.

Otvos et al., "Relationships Between the Proton Nuclear Magnetic Resonance Properties of Plasma Lipoproteins and Cancer", Clin Chem, vol. 37, No. 3, 1991, pp. 369-376.

Soedamah-Muthu et al., The Effect of Atorvastation on Serum Lipids, Lipoproteins and NMR Spectroscopy Defined Lipoprotein Subclasses in Type 2 Diabetic Patients with Ischaemic Heart Disease, Atherosclerosis, Apr. 30, 2003, pp. 243-255, vol. 167, No. 2.

State Intellectual Property Office, P.R. China, "Office Action", Application No. 201380064302, dated Jan. 28, 2016, 15 pages.

State Intellectual Property Office, P.R. China, "Office Action", Application No. 201380041876, dated Mar. 3, 2016.

Wilson et al. "Impact of National Guidelines for Cholesterol Risk Factor Screening, The Framingham Offspring Study", *JAMA*, 1989, 262;41-44.

You et al., "Serum Metabonomics Research on Shenxu-tanyu Syndrome Type 2 Diabetes Mellitus Based on NMR", Science and Technology Review, vol. 30, No. 8, Dec. 31, 2012, pp. 25-29 (English Abstract Only).

U.S. Appl. No. 13/801,604 , "Final Office Action", dated Dec. 9, 2015, 20 pages.

U.S. Appl. No. 13/801,604 , "Non-Final Office Action", dated Apr. 28, 2015, 18 pages.

U.S. Appl. No. 13/801,604 , "Supplemental Non-Final Office Action", dated May 4, 2015, 17 pages.

U.S. Appl. No. 13/830,784 , "Final Office Action", dated Jun. 11, 2015, 9 pages.

U.S. Appl. No. 13/830,784 , "Non-Final Office Action", dated Nov. 25, 2014, 8 pages.

AU Patent Application No. 2013329308 , "First Examination Report", dated Jun. 19, 2018, 4 pages.

AU Patent Application No. 2013329308 , "Notice of Allowance", dated Oct. 17, 2018, 3 pages.

Barclay et al., "Glycemic Index, Glycemic Load, and Chronic Disease Risk—a Meta-analysis of Observational Studies", The American Journal of Clinical Nutrition vol. 87, No. 3, Mar. 2008, pp. 627-637.

CA Patent Application No. 2,874,550 , "Office Action", dated Apr. 2, 2020, 4 pages.

CA Patent Application No. 2,874,550 , "Office Action", dated Apr. 3, 2019, 5 pages.

CA Patent Application No. 2,887,475 , "Office Action", dated Dec. 17, 2019, 6 pages.

Delaglio et al., "Measurement of Homonuclear Proton Couplings from Regular 20 COSY Spectra", Journal of Magnetic Resonance, vol. 149, No. 2, Apr. 2001, pp. 276-281.

EP Patent Application No. 13800239.9 , "Extended European Search Report", dated Jun. 30, 2016, 13 pages.

(56) References Cited

OTHER PUBLICATIONS

EP Patent Application No. 13844778.4, "Extended European Search Report", dated Jun. 1, 2016, 11 pages.
Gao et al., "Metabonomic Profiling of Renal Cell Carcinoma: High-resolution Proton Nuclear Magnetic Resonance Spectroscopy of Human Serum with Multivariate Data Analysis", Anal Chim Acta., vol. 624, No. 2, Aug. 29, 2008, pp. 269-277.
IN Patent Application No. 2583/CHENP/2015, "First Examination Report", dated Sep. 26, 2019, 8 pages.
Lu et al., "Evaluation of Risk Equations for Prediction of Short-term Coronary Heart Disease Events in Patients With Long-standing Type 2 Diabetes: The Translating Research into Action for Diabetes (TRIAD) Study", BMC Endocrine disorders, vol. 12, No. 12, Jul. 9, 2012, pp. 1-10.
O'Connell, "The Complex Role of Branched Chain Amino Acids in Diabetes and Cancer", Metabolites vol. 3, No. 4, Oct. 14, 2013, pp. 931-945.
Pauli et al., "Quantitative 1H NMR. Development and Potential of an Analytical Method: An Update", Journal of Natural Products, vol. 75, No. 4, Apr. 6, 2012, pp. 834-851.
International Patent Application No. PCT/US2012/044679, "International Search Report and Written Opinion", dated Jan. 10, 2013, 9 pages.
International Patent Application No. PCT/US2013/44679, "International Preliminary Report on Patentability", dated Dec. 18, 2014, 13 pages.
SG Patent Application No. 11201407803T, "Written Opinion", dated Jun. 16, 2016, 5 pages.

\* cited by examiner

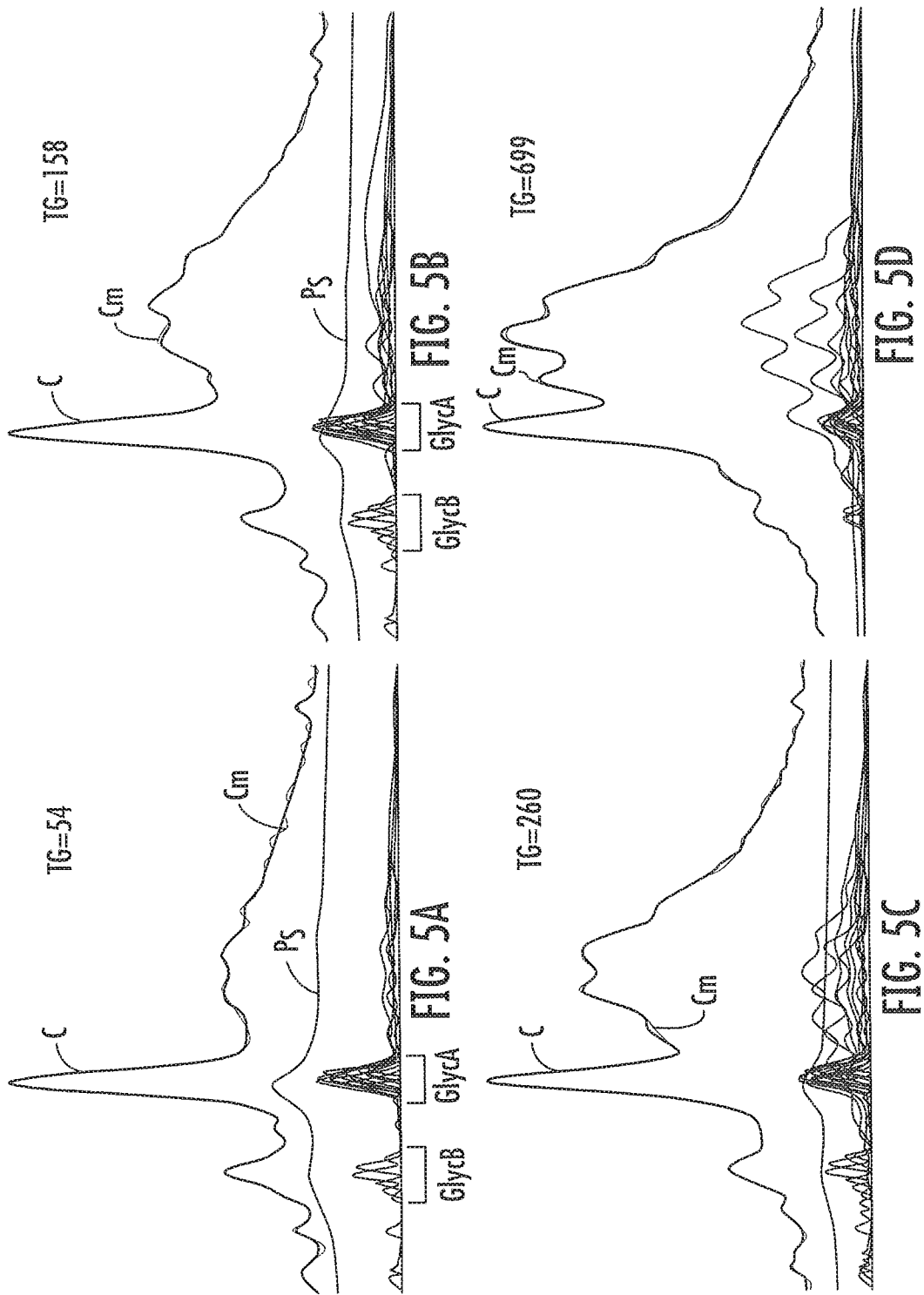

USE OF DIFFERENT PROTEIN COMPONENTS IN THE GlycA DECONVOLUTION MODEL GIVES DIFFERENT GlycA CONCENTRATIONS AND DIFFERENT GlycA ASSOCIATIONS WITH CHD EVENTS AND ALL-CAUSE DEATH IN MESA

| PROTEIN COMPONENT USED IN FITTING MODEL | GlycA CONCENTRATION | CHD EVENT PREDICTION | | ALL-CAUSE DEATH PREDICTION | |
|---|---|---|---|---|---|
| | $\mu mol/L$ | $\chi^2$ | p | $\chi^2$ | p |
| PROTEIN #1 | 342 | 13.1 | 0.0003 | 23.1 | <0.0001 |
| PROTEIN #2 | 186 | 12.7 | 0.0004 | 11.2 | 0.0008 |
| PROTEIN #3 | 162 | 10.9 | 0.0003 | 7.4 | 0.007 |

Fig. 7B

| Component ID | Component Class | Chemical Shift (ppm) | Component ID | Component Class | Chemical Shift (ppm) | Component ID | Component Class | Chemical Shift (ppm) |
|---|---|---|---|---|---|---|---|---|
| AA1 | Metabolite A | 1.875040 | VLDL7 | VLDL | 1.966840 | GLYC21 | | 2.019880 |
| AA2 | Metabolite A | 1.876400 | VLDL8 | VLDL | 1.968200 | GLYC22 | | 2.021240 |
| AA3 | Metabolite A | 1.876400 | VLDL9 | VLDL | 1.969560 | GLYC23 | | 2.022600 |
| AA4 | Metabolite A | 1.876400 | VLDL10 | VLDL | 1.970920 | GLYC24 | | 2.023960 |
| AA5 | Metabolite A | 1.877760 | VLDL11 | VLDL | 1.971600 | GLYC25 | | 2.025320 |
| AA6 | Metabolite A | 1.879120 | VLDL12 | VLDL | 1.973640 | GLYC26 | | 2.026680 |
| AA7 | Metabolite A | 1.880480 | VLDL13 | VLDL | 1.975000 | GLYC27 | | 2.028040 |
| HDL1 | HDL | 1.915840 | VLDL14 | VLDL | 1.976360 | GLYC28 | | 2.029400 |
| HDL2 | HDL | 1.918560 | VLDL15 | VLDL | 1.975680 | GLYC29 | | 2.030760 |
| HDL3 | HDL | 1.919240 | VLDL16 | VLDL | 1.977040 | GLYC30 | | 2.032120 |
| HDL4 | HDL | 1.919920 | CHY1 | CHYLOS | 1.978400 | GLYC31 | | 2.034840 |
| HDL5 | HDL | 1.920600 | CHY2 | CHYLOS | 1.979080 | GLYC32 | | 2.037560 |
| HDL6 | HDL | 1.921280 | CHY3 | CHYLOS | 1.979760 | GLYC33 | | 2.040280 |
| HDL7 | HDL | 1.925360 | CHY4 | CHYLOS | 1.980440 | GLYC34 | | 2.043000 |
| HDL8 | HDL | 1.928760 | CHY5 | CHYLOS | 1.981120 | GLYC35 | | 2.045720 |
| HDL9 | HDL | 1.930800 | CHY6 | CHYLOS | 1.981800 | GLYC36 | | 2.048440 |
| HDL10 | HDL | 1.933520 | CHY7 | CHYLOS | 1.982480 | GLYC37 | | 2.051160 |
| HDL11 | HDL | 1.934880 | CHY8 | CHYLOS | 1.983160 | GLYC38 | | 2.053880 |
| HDL12 | HDL | 1.936240 | CHY9 | CHYLOS | 1.983840 | GLYC39 | | 2.056600 |
| HDL13 | HDL | 1.936920 | CHY10 | CHYLOS | 1.984520 | GLYC40 | | 2.059320 |
| HDL14 | HDL | 1.937600 | CHY11 | CHYLOS | 1.985200 | GLYC41 | | 2.062040 |
| HDL15 | HDL | 1.938280 | CHY12 | CHYLOS | 1.985880 | GLYC42 | | 2.064760 |
| HDL16 | HDL | 1.938960 | GLYC1 | | 1.992680 | GLYC43 | | 2.067480 |
| HDL17 | HDL | 1.939640 | GLYC2 | | 1.994040 | GLYC44 | | 2.070200 |
| HDL18 | HDL | 1.941000 | GLYC3 | | 1.995400 | GLYC45 | | 2.072920 |
| HDL19 | HDL | 1.941680 | GLYC4 | | 1.996760 | GLYC46 | | 2.075640 |
| HDL20 | HDL | 1.943040 | GLYC5 | | 1.998120 | Protein | | |
| LDL1 | LDL | 1.947800 | GLYC6 | | 1.999480 | | | |
| LDL2 | LDL | 1.948480 | GLYC7 | | 2.000840 | | | |
| LDL3 | LDL | 1.949160 | GLYC8 | | 2.002200 | | | |
| LDL4 | LDL | 1.949840 | GLYC9 | | 2.003560 | | | |
| LDL5 | LDL | 1.950520 | GLYC10 | | 2.004920 | | | |
| LDL6 | LDL | 1.951200 | GLYC11 | | 2.006280 | | | |
| LDL7 | LDL | 1.952560 | GLYC12 | | 2.007640 | | | |
| LDL8 | LDL | 1.953920 | GLYC13 | | 2.009000 | | | |
| LDL9 | LDL | 1.955280 | GLYC14 | | 2.010360 | | | |
| VLDL1 | VLDL | 1.960040 | GLYC15 | | 2.011720 | | | |
| VLDL2 | VLDL | 1.961400 | GLYC16 | | 2.013080 | | | |
| VLDL3 | VLDL | 1.962760 | GLYC17 | | 2.014440 | | | |
| VLDL4 | VLDL | 1.964120 | GLYC18 | | 2.015800 | | | |
| VLDL5 | VLDL | 1.965480 | GLYC19 | | 2.017160 | | | |
| VLDL6 | VLDL | 1.966160 | GLYC20 | | 2.018520 | | | |

Fig. 7C
Fig. 7D
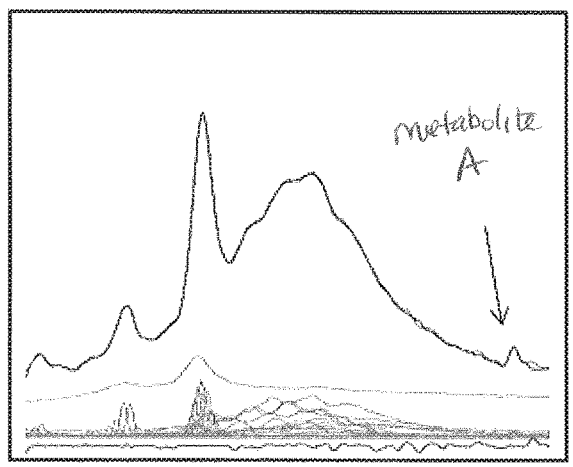
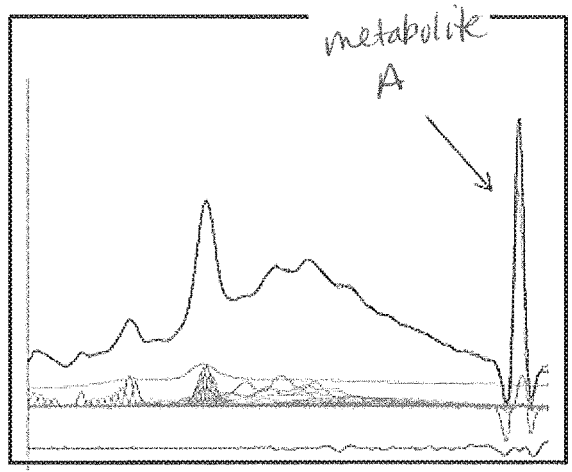

PROSPECTIVE ASSOCIATIONS OF NMR-MEASURED GlycA AND VALINE LEVELS AND HS-CRP WITH SELECTED DISEASE OUTCOMES IN MESA (n~5680)

| | GlycA | | hs-CRP | | VALINE | | GlycA+VALINE |
|---|---|---|---|---|---|---|---|
| | $\chi^2$ | p | $\chi^2$ | p | $\chi^2$ | p | $\chi^2$ |
| CHD EVENTS (N=289) | 7.0 | 0.007 | 3.1 | ns | 0.3 | ns | 7.8 |
| ALL-CAUSE DEATH (N=346) | 24.8 | <0.0001 | 13.9 | 0.0003 | 14.4 | 0.0002 | 36.7 |
| CONGESTIVE HEART FAILURE (N=149) | 2.5 | ns | 2.9 | ns | 12.3 | 0.0006 | 14.1 |
| STROKE (N=117) | 1.3 | ns | 0 | ns | 0 | ns | 1.4 |
| CHRONIC KIDNEY DISEASE (N=181) | 29.3 | <0.0001 | 3.4 | 0.05 | 2.9 | ns | 31.0 |
| COPD (N=120) | 20.5 | <0.0001 | 3.6 | 0.03 | 6.7 | 0.01 | 26.3 |
| CANCER (N=440) | 8.0 | 0.004 | 3.0 | ns | 3.8 | 0.05 | 11.3 |
| ASTHMA (N=154) | 3.5 | 0.06 | 1.6 | ns | 2.0 | ns | 6.2 |
| DEMENTIA (N=71) | 5.8 | 0.01 | 0 | ns | 3.9 | 0.05 | 10.0 |
| DIABETES (N=493) | 10.3 | 0.001 | 4.7 | 0.04 | 29.0 | <0.0001 | 40.3 |

FIG. 9

CHARACTERISTICS OF MESA SUBJECTS BY GlycA QUARTILE

|  | GlycA QUARTILE | | | |
|---|---|---|---|---|
|  | 1 | 2 | 3 | 4 |
| GlycA | 21.6 | 25.8 | 29.3 | 35.3 |
| hsCRP (mg/L) | 1.3 | 2.2 | 3.8 | 7.6 |
| SMOKING (%) | 9 | 11 | 13 | 17 |
| HYPERTENSION (%) | 34 | 41 | 47 | 55 |
| DIABETES (%) | 8.1 | 10.8 | 12.8 | 18.8 |
| MetSyn (%) | 20 | 31 | 39 | 55 |
| LP-IR SCORE | 35 | 44 | 46 | 52 |

FIG. 11

INDEPENDENT ASSOCIATIONS OF INFLAMMATION MARKERS WITH CHD EVENTS IN MESA

| N=5607<br>289 CHD EVENTS | $\chi^2$ MODEL | HR per 1SD | $c^2$ PARAM | P |
|---|---|---|---|---|
| BASE MODEL | 235.4 | --- | --- | --- |
| hsCRP | 239.1 | 1.07 | 1.8 | ns |
| FIBRINOGEN | 238.5 | 1.15 | 5.4 | 0.02 |
| GlycA | 244.9 | 1.21 | 10.4 | 0.001 |

COX MODELS ADJUSTED FOR AGE, SEX, ETHNICITY, SMOKING, SBP, HYPERTENSION MEDICATION, BMI, DIABETES, LDL-P, AND HDL-P

FIG. 12

ASSOCIATIONS WITH ALL-CAUSE DEATH IN MESA

| N=5607<br>345 DEATHS | $\chi^2$ MODEL | HR per 1SD | $c^2$ PARAM | P |
|---|---|---|---|---|
| BASE MODEL | 338.0 | --- | --- | --- |
| TC, LDL-C, LDL-P |  |  |  | ns |
| HDL-C | 342.9 | 0.90 | 2.6 | ns |
| CRP | 352.8 | 1.15 | 19.2 | <0.0001 |
| FIBRINOGEN | 350.7 | 1.21 | 13.8 | 0.0002 |
| HDL-P | 356.1 | 0.76 | 17.5 | <0.0001 |
| GlycA | 363.8 | 1.30 | 30.2 | <0.0001 |
| HDL-P/GlycA | 378.7 | 0.68 | 38.6 | <0.0001 |

COX MODELS ADJUSTED FOR AGE, SEX, ETHNICITY, SMOKING, SBP, HYPERTENSION MEDICATION, BMI, AND DIABETES

FIG 13

PREDICTION OF ALL-CAUSE DEATH IN MESA (n=5712)*

| PARAMETER | MODEL $\chi^2$ | c-STATISTIC | PARAMETER | PARAMETER $\chi^2$ | P |
|---|---|---|---|---|---|
| BASE MODEL COVARIATES | 330.7 | 0.770 | | | |
| + TC/HDL-C | 335.5 | 0.773 | | 2.68 | 0.1 |
| + hsCRP | 346.9 | 0.776 | | 16.6 | <0.0001 |
| + VALINE | 348.5 | 0.777 | | -17.4 | <0.0001 |
| + GlycA | 354.0 | 0.778 | | 23.9 | <0.0001 |
| + HDL-P | 347.7 | 0.777 | | -16.4 | <0.0001 |
| + HDL-P/GlycA | 367.4 | 0.782 | | -34.8 | <0.0001 |
| + HDL-P*VALINE | 360.7 | 0.780 | | -28.4 | <0.0001 |
| + HDL-P*VALINE + GlycA | 384.9 | 0.788 | HDL-P*VALINE | -29.2 | <0.0001 |
| | | | GlycA | 24.6 | <0.0001 |
| +HDL-P+VALINE+GlycA | 388.5 | 0.789 | HDL-P | -15.6 | <0.0001 |
| | | | VALINE | -16.9 | <0.0001 |
| | | | GlycA | 24.4 | <0.0001 |
| + (HDL-P*VALINE)/GlycA | 382.2 | 0.786 | | -47.6 | <0.0001 |

*PREDICTION OF ALL-CAUSE DEATH (n=346) FROM LOGISTIC REGRESSION ANALYSES (ADJUSTED).

FIG. 24

NMR MEASUREMENTS OF NMR BIOMARKER GLYCA

RELATED APPLICATIONS

This application is a continuation application of U.S. patent application Ser. No. 13/830,199, filed Mar. 14, 2013, which claims the benefit of and priority to U.S. Provisional Patent Application No. 61/657,315, filed Jun. 8, 2012, U.S. Provisional Patent Application No. 61/711,471, filed Oct. 9, 2012, and U.S. Provisional Patent Application No. 61/739,305, filed Dec. 19, 2012, the disclosures of which are herein incorporated in their entirety.

FIELD OF THE INVENTION

The present invention relates generally to analysis of in vitro biosamples. The invention may be particularly suitable for NMR analysis of human blood plasma and serum.

BACKGROUND OF THE INVENTION

Conventionally, a patient's overall risk of coronary heart disease (CHD) and/or coronary artery disease (CAD) has been assessed based on measurements of cholesterol content of a patient's low density lipoproteins (LDL) and high density lipoproteins (HDL) (LDL-C, HDL-C) rather than the numbers of LDL and HDL particles. LDL-C and HDL-C are used to assess a patient's CHD risk and treatment decisions may be made to reduce the "bad" cholesterol (LDL-C) and/or increase the "good" cholesterol (HDL-C).

A "C-reactive protein" (CRP) test is a blood test that measures the amount of CRP protein in a blood sample. C-reactive protein is thought to measure general levels of inflammation in a patient's body. One type of CRP test, termed a high-sensitivity CRP test (hs-CRP), may be performed to find out if a person has an increased risk of having a heart attack.

NMR spectroscopy has been used to concurrently measure very low density lipoprotein (VLDL), LDL and HDL as VLDL, LDL and HDL particle subclasses from in vitro blood plasma or serum samples. See, U.S. Pat. Nos. 4,933,844 and 6,617,167, the contents of which are hereby incorporated by reference as if recited in full herein. Generally stated, to evaluate the lipoproteins in a blood plasma and/or serum sample, the amplitudes of a plurality of NMR spectroscopy derived signals within a chemical shift region of NMR spectra are derived by deconvolution of the composite methyl signal envelope to yield subclass concentrations. The subclasses are represented by many (typically over 60) discrete contributing subclass signals associated with NMR frequency and lipoprotein diameter. The NMR evaluations can interrogate the NMR signals to produce concentrations, of different subpopulations, typically seventy-three discrete subpopulations, 27 for very low density lipoproteins (VLDL), 20 for LDL and 26 for HDL. These sub-populations can be further characterized as associated with a particular size range within the VLDL, LDL or HDL subclasses.

In the past, an "advanced" lipoprotein test panel, such as the LIPOPROFILE® lipoprotein test, available from LipoScience, Raleigh, N.C., has typically included a total high density lipoprotein particle (HDL-P) measurement (e.g., HDL-P number) that sums the concentration of all the HDL subclasses and a total low density lipoprotein particle (LDL-P) measurement that sums the concentration of all the LDL subclasses (e.g., LDL-P number). The LDL-P and HDL-P numbers represent the concentration of those respective particles in concentration units such as nmol/L.

Inflammation can be associated with many different disease states including, but not limited to, CHD. It is also believed that inflammation may modulate HDL functionality, See, e.g., Fogelman, When Good Cholesterol Goes Bad, Nature Medicine, 2004. Carbohydrate components of glycoproteins can perform biological functions in protein sorting, immune and receptor recognition, inflammation and other cellular processes. There can also be variations in structure and differing degrees of glycosylation. See, Gates et al., Glycoprotein Analysis Manual, Overview, 1$^{st}$ edition, 2004, Sigma Aldrich, www.sismaaldrich.com/img/assests/15402/Glycoprotein. The contents of the above referenced documents are hereby incorporated by reference as if recited in full herein.

In the past, life insurance companies have considered various information regarding a prospective customer to identify whether to insure a person and at what price. One input used by some companies to predict a risk of all cause death for such analysis is a ratio of total cholesterol to HDL-C. However, it is believed that this is a relatively poor predictor of all-cause death.

SUMMARY

Embodiments of the invention identify a novel NMR-derived biomarker termed "GlycA" based on deconvolution of a defined region of an NMR spectrum of a blood plasma or serum sample.

Embodiments of the invention identify a novel NMR-derived biomarker termed "GlycB" based on deconvolution of a defined region of an NMR spectrum of a blood plasma or serum sample.

Embodiments of the invention provide multiple-parameter risk assessments and/or screenings using GlycA and one or both of (i) Valine and (ii) at least one lipoprotein subclass input.

Embodiments of the invention provide multiple-parameter all-cause death risk assessments and/or screenings using GlycA and one or both of (i) Valine and (ii) at least one lipoprotein input, such as HDL-P.

Embodiments of the invention evaluate an in vitro biosample to calculate all-cause death risk using the equation: HDL-P*Valine/GlycA.

The computer program product may include computer readable program code that applies a conversion factor to the summed Lorentzian functions to generate the measurement of GlycA in µmol/L.

The computer program product can include computer readable program code that compares the GlycA measurement to a predefined range of measurements having associated degrees of CHD risk.

The computer program product can include computer readable program code that generates a patient report with the GlycA measurement and an associated with risk assessment.

The computer program code that provides the measurement can be configured to evaluate NMR spectra of an in vitro blood plasma or serum patient sample using NMR signal having a peak centered at about 2.00 ppm.

Still other embodiments are directed to systems that include: an NMR spectrometer for acquiring at least one NMR spectrum of an in vitro biosample; and at least one processor in communication with the NMR spectrometer, the at least one processor configured to obtain NMR measurement of GlycA using the at least one NMR spectrum.

The at least one processor can be configured to: (i) obtain a composite NMR spectrum of a fitting region of an in vitro plasma biosample; (ii) deconvolve the composite NMR spectrum using a defined deconvolution model with high density lipoprotein (HDL) components, low density lipoprotein (LDL) components, VLDL (very low density lipoprotein)/chylomicron components, a defined protein signal component, and curve fit functions associated with at least a GlycA peak region; and (iii) electronically sum a defined number of the functions to generate the NMR measurement of GlycA.

The curve fit functions can comprise Lorentzian and/or other suitable functions.

The at least one processor can be configured to apply a conversion factor to the summed NMR measurement to generate a GlycA measurement in μmol/L.

The biosample can be a blood plasma or serum sample. The at least one processor is configured to obtain a concentration measurement of high density lipoprotein particles (HDL-P) and a concentration measurement of low density lipoprotein particles (LDL-P).

The at least one processor is configured to generate patient reports summarizing the respective LDL-P, HDL-P and GlycA measurements.

Yet other embodiments are directed to a patient report that includes a plurality of lipoprotein measurements including a quantitative measure of GlycA μmol/L and/or arbitrary units and at least one of: (i) a low density lipoprotein particle number (LDL-P) in concentration units and (ii) a high density lipoprotein particle (HDL-P) number in concentration units.

The patient report can also includes at least one of NMR measures of magnesium and/or valine.

Yet other embodiments are directed to NMR analyzers. The NMR analyzers include: a NMR spectrometer; a flow probe in communication with the spectrometer; and a controller in communication with the spectrometer configured to obtain NMR signal of a defined single peak region of NMR spectra associated with GlycA of a fluid specimen in the flow probe and generate a patient report providing a GlycA level.

The controller can include or be in communication with at least one local or remote processor, wherein the at least one processor is configured to: (i) obtain a composite NMR spectrum of a fitting region of an in vitro plasma biosample; (ii) deconvolve the composite NMR spectrum using a defined deconvolution model with high density lipoprotein (HDL) components, low density lipoprotein (LDL) components, VLDL(very low density lipoprotein)/chylomicron components, a defined protein signal component, and curve fit functions (e.g., overlapping Lorentzian functions) applied to at least a GlycA peak region; and (iii) electronically sum a defined number of the applied Lorentzian functions to generate the GlycA level.

The at least one processor can be configured to apply a conversion factor to the summed NMR measurement to generate a GlycA measurement in μmol/L.

In some embodiments, NMR measures of NMR signal in a defined peak region of proton NMR spectrum associated with GlycA can be determined. The GlycA signal measurement can be used as an inflammation biomarker for assessing CHD risk.

The NMR signal for GlycA can include signal associated with N-acetylglucosylated proteins at between about 2.080 ppm and 1.845 ppm of the proton NMR spectra of blood plasma or serum (typically at 47 deg. C.+/−0.2).

The at least one processor can be configured to use the GlycA measurement as a denominator in a defined all-cause death risk ratio to generate a risk predictor associated with a risk of all-cause death.

It is believed that human plasma GlycA is more independent and a stronger inflammation biomarker for CHD/heart attack risk than hs-CRP, particularly when risk correlation is adjusted for other confounding factors (e.g., systolic blood pressure, age, gender, BMI, diabetes and smoking).

A patient's risk of having or developing CHD and/or a heart attack can be evaluated using a plurality of NMR derived measurements including LDL-P, HDL-P and GlycA.

Embodiments of the invention can generate a patient report that includes a calculated ratio of measurements of valine, HDL-P and GlycA using the ratio: (Valine*HDL-P)/GlycA.

The method can include electronically calculating LDL-P and HDL-P from NMR spectra of the biosample and the determining step can include identifying an increased risk of CHD when GlycA and LDL-P are above a respective population norm and HDL-P is below a population norm.

Some embodiments are directed to methods to evaluate or predict all-cause death risk of a person. The methods include: (a) electronically calculating a ratio of measurements of at least one of the following; Valine to GlycA, HDL-P to GlycA or (Valine*HDL-P)/GlycA; and (b) evaluating whether a person has an increased risk for all-cause death relative to a population, wherein a respective person has increased risk relative to a population when the calculated ratio is in a first tertile, quartile or quintile of the population. The calculating can be carried out using the ratio of (Valine*HDL-P)/GlycA.

Further features, advantages and details of the present invention will be appreciated by those of ordinary skill in the art from a reading of the figures and the detailed description of the preferred embodiments that follow, such description being merely illustrative of the present invention. Features described with respect with one embodiment can be incorporated with other embodiments although not specifically discussed therewith. That is, it is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. The foregoing and other aspects of the present invention are explained in detail in the specification set forth below.

As will be appreciated by those of skill in the art in light of the present disclosure, embodiments of the present invention may include methods, systems, apparatus and/or computer program products or combinations thereof.

BRIEF DESCRIPTION OF THE FIGURES

FIGS. 5A-5D are GlycA/B NMR spectral regions illustrating spectral overlap from lipoprotein signals (from especially VLDL/Chylos) for samples with high TG (triglycerides).

FIG. 7B is a table of components in a GlycA/B deconvolution model according to embodiments of the present invention.

FIG. 7C is an NMR spectrum showing metabolite A present in a sample at typical normal (low) concentration according to embodiments of the present invention.

FIG. 7D is an NMR spectrum showing metabolite A present in a sample at an elevated (high) concentration according to embodiments of the present invention.

FIG. 8A is from the MESA study of apparently healthy men and women. FIG. 8B is from a study of women with Rheumatoid Arthritis.

FIG. 9 is a chart of prospective associations of hs-CRP and NMR-measured GlycA and NMR-measured valine levels with various disease outcomes in MESA (n=5680) according to embodiments of the present invention.

FIG. 11 is a chart of characteristics of MESA subjects by NMR measured GlycA quartile (in "NMR signal area units") according to embodiments of the present invention.

FIG. 12 is a chart showing the independent associations of hsCRP, fibrinogen, and GlycA with future CHD events in MESA according to embodiments of the present invention.

FIG. 13 is a table of various statistical evaluations of the associations with all-cause death in MESA (345 deaths, N=5607) of various parameters including lipids, lipoproteins, inflammation markers, and GlycA when added to a base prediction model including 8 covariates according to embodiments of the present invention.

FIG. 24 is a table from logistic regression analyses adjusted for age, gender, race, smoking, systolic blood pressure, hypertension medications, body mass index, diabetes and LDL-P illustrating all cause death prediction according to embodiments of the present invention.

DETAILED DESCRIPTION OF EMBODIMENTS OF THE INVENTION

Figure 1:
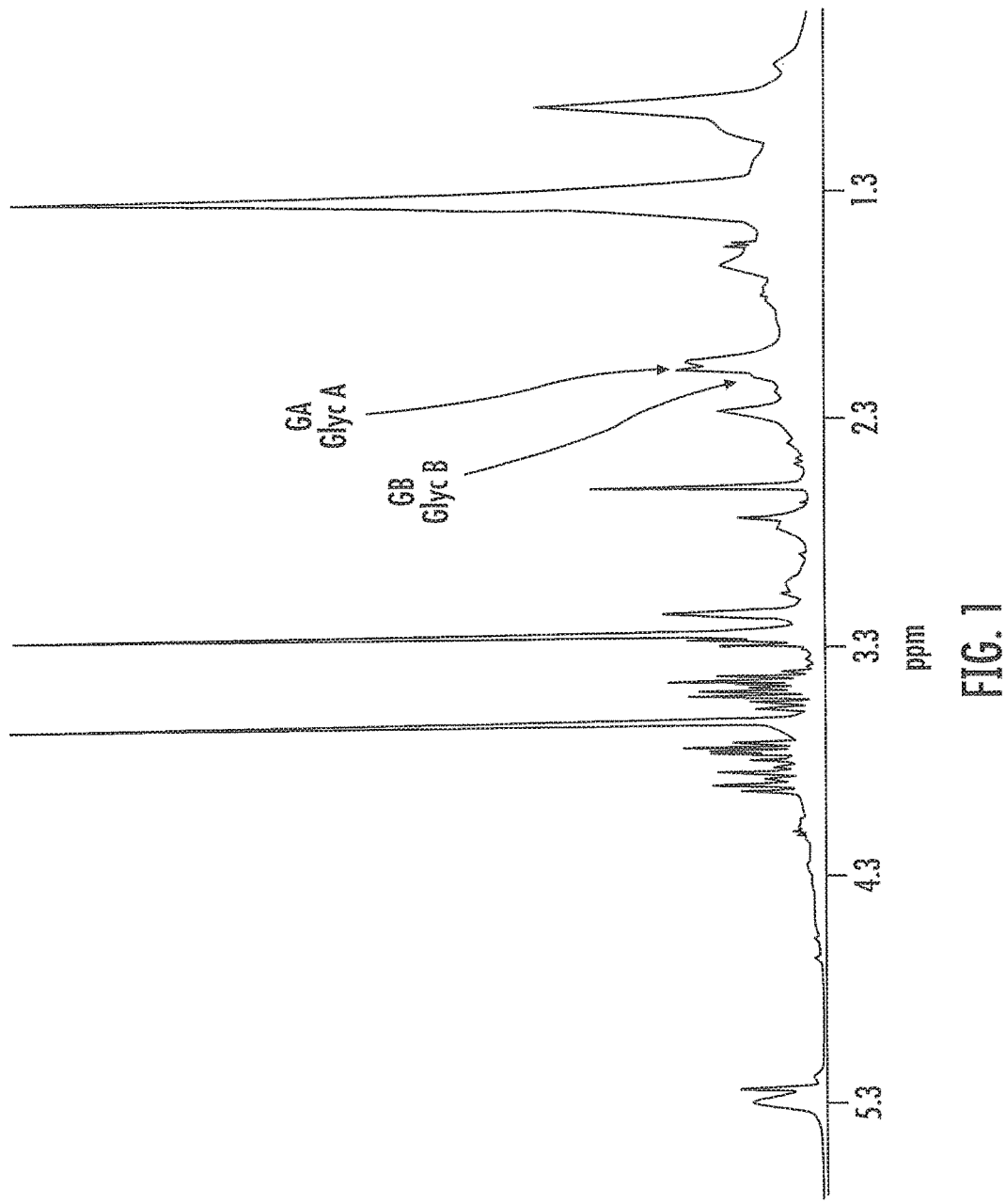
FIG. 1 is a an NMR spectrum showing the inflammation markers in the exemplary plasma NMR spectrum (N-acetyl methyl signals from glycosylated acute phase proteins, GlycA and GlycB, respectively) according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about V." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail fir brevity and/or clarity.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "programmatically" means carried out using computer program and/or software, processor or ASIC directed operations. The term "electronic" and derivatives thereof refer to automated or semi-automated operations carried out using devices with electrical circuits and/or modules rather than via mental steps and typically refers to operations that are carried out programmatically. The terms "automated" and "automatic" means that the operations can be carried out with minimal or no manual labor or input. The term "semi-automated" refers to allowing operators some input or activation, but the calculations and signal acquisition as well as the calculation of the concentrations of the ionized constituent(s) is done electronically, typically programmatically, without requiring manual input. The term "about" refers to +/−10% (mean or average) of a specified value or number.

The terms "CAD" and "CHD" are used interchangeably to correspond to a patient or subject's risk of developing or having coronary artery and/or coronary heart disease, respectively. The term cardio vascular disease (CVD) refers to a combined outcome that is typically CHD plus stroke.

The term "all-cause death" refers to dying for any reason, either as a result of a disease such as CHD or cancer, or accident, or natural causes such as old age.

The term "GlycA" refers to a new biomarker that is derived from a measure of composite NMR signal from carbohydrate portions of acute phase reactant glycoproteins containing N-acetylglucosamine and/or N-acetylgalactosamine moieties, more particularly from the protons of the 2-NAcGlc and 2-NAcGal methyl groups. The GlycA signal is centered at about 2.00 ppm in a plasma NMR spectrum at about 47 deg C. The peak location is independent of spectrometer field but may vary depending on analysis temperature of the biosample. Thus, the GlycA peak region may vary if the temperature of the test sample varies. The GlycA NMR signal may include a subset of NMR signal at the defined peak region so as to include only clinically relevant signal contributions and may exclude a protein contribution to the signal in this region as will be discussed further below.

The term "GlycB" refers to a new biomarker that is derived from a measure of composite NMR signal from the carbohydrate portions of acute phase reactant glycoproteins containing N-acetylneuraminic acid (sialic acid) moieties, more particularly from the protons of the 5-N-acetyl methyl groups. The GlycB signal is centered at about 2.04 ppm in the plasma NMR spectrum at about 47 deg C. The peak location is independent of spectrometer field but may vary depending on analysis temperature of the biosample. Thus, the GlycB peak region may vary if the temperature of the test sample varies.

As used herein, the chemical shift locations (ppm) refer to NMR spectra referenced internally to CaEDTA signal at 2.519 ppm. Thus, the noted peak locations discussed and/or claimed herein may vary depending on how the chemical shift is generated or referenced as is well known to those of skill in the art Thus, to be clear, certain of the described and/or claimed peak locations have equivalent different peak locations in other corresponding chemical shifts as is well known to those of skill in the art.

The term "biosample" refers to in vitro blood, plasma, serum, CSF, saliva, lavage, sputum, or tissue samples of humans or animals. Embodiments of the invention may be particularly suitable for evaluating human blood plasma or serum biosamples. The blood plasma or serum samples may be fasting or non-fasting. GlycA and GlycB are not found in urine and are most suitable for evaluation in blood plasma or serum samples.

The terms "population norm" and "standard" refer to values defined by a large study or studies such as the Framingham Offspring Study or the Multi-Ethnic Study of Atherosclerosis (MESA) or other study having a large enough sample to be representative of the general population. However, the instant invention is not limited to the population values in MESA as the presently defined normal and at-risk population values or levels may change over time. Thus, a reference range associated with values from a defined population can be provided and used to assess elevated or reduced levels and/or risk of having a clinical disease state.

The term "patient" is used broadly and refers to an individual that provides a biosample for testing or analysis.

The term "clinical disease state" means an at-risk medical condition that may indicate medical intervention, therapy, therapy adjustment or exclusion of a certain therapy (e.g., pharmaceutical drug) and/or monitoring is appropriate. Identification of a likelihood of a clinical disease state can allow a clinician to treat, delay or inhibit onset of the condition accordingly. Examples of clinical disease states include, but are not limited to, CHD, CVD, stroke, type 2 diabetes, prediabetes, dementia, Alzheimers, cancer, arthritis, rheumatoid arthritis (RA), kidney disease, pulmonary disease, COPD (chronic obstructive pulmonary disease), peripheral vascular disease, congestive heart failure, organ transplant response, and/or medical conditions associated with immune deficiency, abnormalities in biological functions in protein sorting, immune and receptor recognition, inflammation, pathogenicity, metastasis and other cellular processes.

The term "HDL-P" refers to a high density lipoprotein particle (HDL-P) measurement (e.g., HDL-P number) that sums the concentration of defined HDL subclasses. HDL-P can include a total high density lipoprotein particle (HDL-P) measurement that sums the concentration μmol/L) of all the HDL subclasses (large, medium and small) in the size range between about 7 nm to about 14 nm. In some embodiments, the HDL-P measurement may employ selected combinations of the HDL subclasses in the noted size range.

As is known to those of skill in the art, valine is an α-amino acid with the chemical formula $HO_2CCH(NH_2)CH(CH_3)_2$. When measured by NMR, the value can be unitless. The valine measurement may be multiplied by a defined conversion factor to convert the value into concentration units. The current Valine embodiment has a conversion factor of 2271 to report Valine in μM units; however, this value can vary by ±10% without unduly affecting the reported value significantly.

Embodiments of the invention use NMR quantified measures of GlycA of a biosample with a measure of valine and/or at least one lipoprotein subclass to screen for and/or identify a likelihood of a subject's health risk such as, but not limited to, a predictor of a subject's risk of all-cause death.

GlycA can be represented by a single peak region centered at about 2.00 ppm (at 47 degrees C.+/−0.2) in plasma NMR spectra. The peak region location may change with temperature.

It is believed that GlycA and/or GlycB are responsive to global protein glycosylation level and can reflect global inflammation status. NMR measures of GlycA, alone or with measures of other defined analytes, or ratios of GlycA/GlycB (or vice versa) can be performed as a standard screening test to identify at-risk individuals or subjects.

GlycA, on its own, may indicate a global measure of inflammation that may be non-specific with respect to a clinical disease state, but such value, particularly when combined with other defined patient-specific parameters may still be a better predictor of all-cause death than conventional total-cholesterol (TC/HDL-C ratios. See, e.g., the discussion below with respect to FIGS. 24 and 25A/25B, for example.

GlycA has a positive correlation with death. To evaluate a risk of all-cause death, other parameters can be evaluated using an in vitro biosample (the same biosample used to evaluate the GlycA or a different biosample). One or more of the other parameters can have negative correlations with death. Thus, embodiments of the invention employ a multi-parameter risk equation and/or an all cause death (ACD) risk ratio that includes GlycA and at least one parameter that has a negative correlation with death, such as, for example valine and/or HDL-P. In this embodiment, the risk evaluation equation can comprise a ratio of HDL-P/GlycA and/or Valine/GlycA, for example.

Embodiments of the invention use a multi-parameter equation that includes: (i) an NMR measure of GlycA; (ii) a measure of valine (which may also be measured by NMR or by other analytic tests); and (iii) at least one other lipoprotein (subclass) parameter which may also be measured by NMR or by other analytic tests). The calculation can provide a risk predictor for all-cause death. The at least one other lipoprotein parameter can be HDL-P.

The multi-parameter equation can be defined by Equation 1.

$$(HDL\text{-}P*Valine)/GlycA \qquad \text{Equation 1}$$

HDL-P can be in μmol/L units. Valine and/or GlycA can be in arbitrary units or one or each can be multiplied by a respective defined conversion factor to provide the number in units of μmol/L (see, e.g., FIG. 7A).

It is contemplated that such a multi-parameter value can also be used to monitor subjects in clinical trials and/or on drug therapies and/or to monitor for changes in risk status (positive or negative) that may be associated with a particular drug, a patient's lifestyle and the like, which may be patient-specific.

The flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks might occur out of the order noted in the figures. For example, two blocks shown in succession may in fact be executed substantially concurrently or the blocks may sometimes be executed in the reverse order, depending upon the functionality involved.

FIG. 1 illustrates the resonant peak regions for GA associated with GlycA and GB associated with GlycB in the plasma NMR spectrum. One or both of these peak regions can include signal that can be defined as inflammation markers in the plasma NMR spectrum.

Figure 2A:
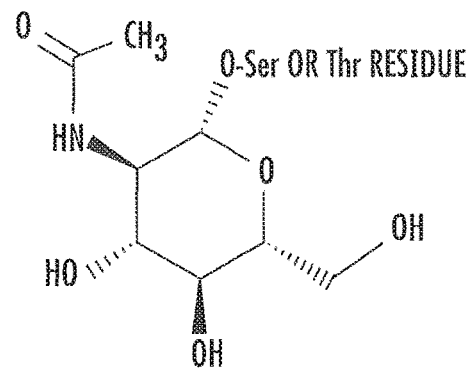
FIGS. 2A and 2B are schematic illustrations of the chemical structures of the carbohydrate portion of N-acetylglycosylated proteins showing the CH3 group that gives rise to the GlycA NMR signal.
Figure 2B:
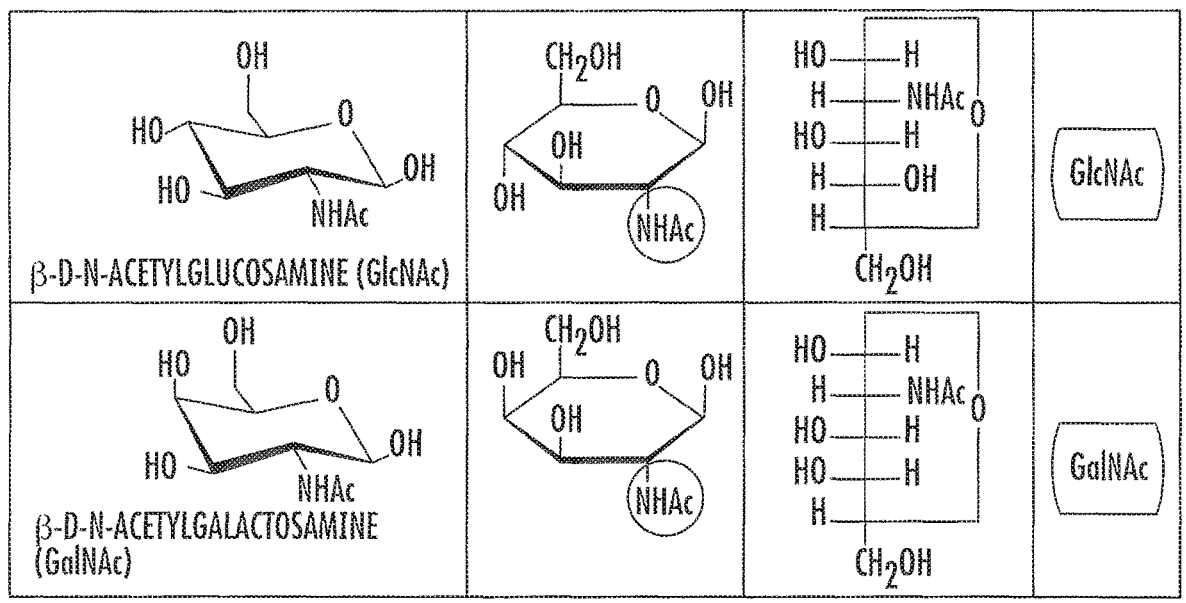
Figure 3A:
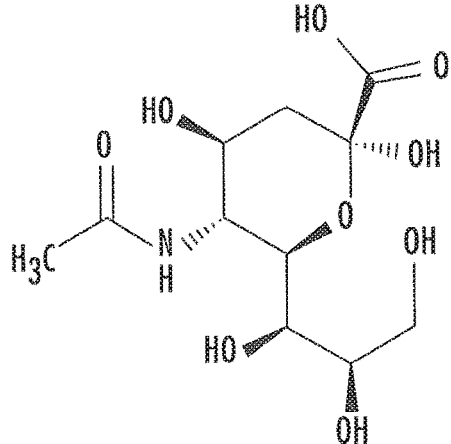
FIGS. 3A and 3B are schematic illustrations of the chemical structures of the carbohydrate portion of N-acetylneuraminie acid (also called sialic acid) modified glycoproteins showing the CH3 group that gives rise to the GlycB NMR signal.
Figure 3B:
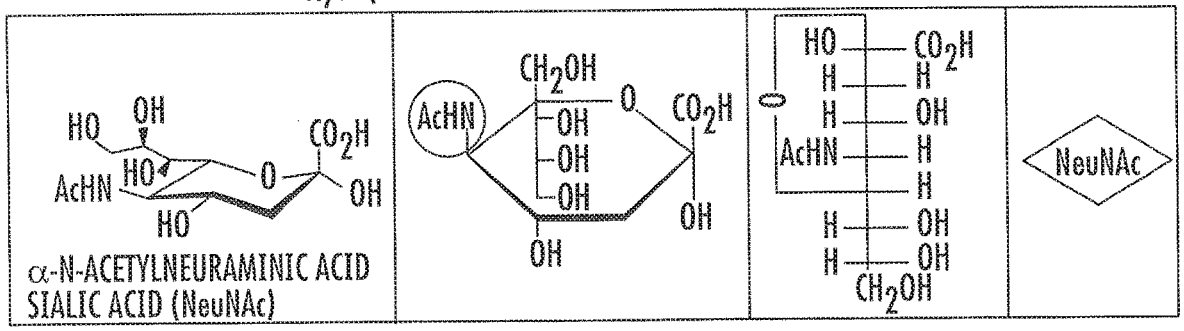

FIGS. 2A/2B illustrates the chemical structure of the carbohydrate portion of N-acetylgtycosylated proteins showing the $CH_3$ group that gives rise to the GlycA NMR signal. FIGS. 3A/3B illustrates the chemical structure of the carbohydrate portion of N-acetylneuraminic acid (also called sialic acid) modified glycoproteins showing the CH3 group that gives rise to the GlycB NMR signal.

Figure 4A:
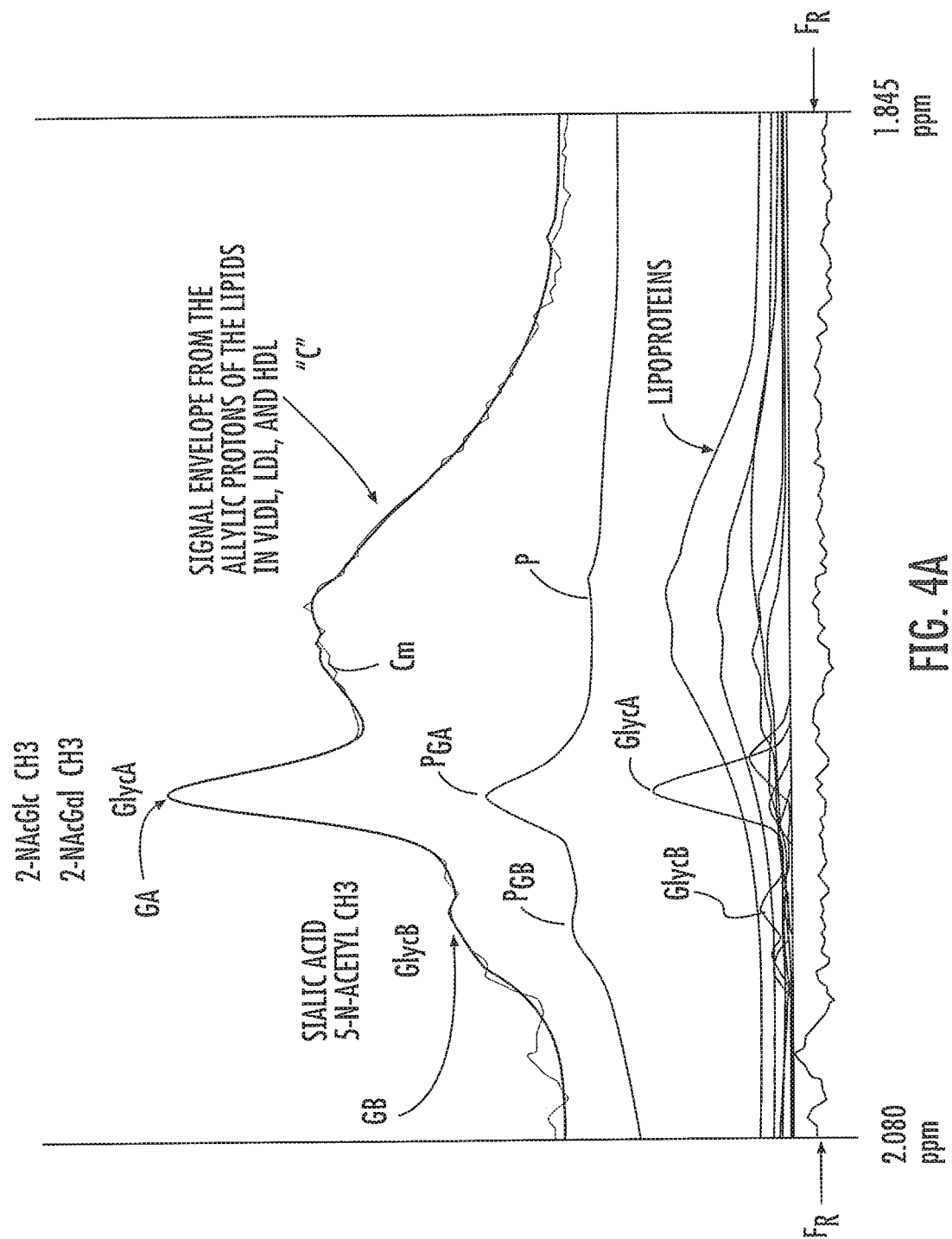
FIG. 4A is a an expansion of the plasma NMR spectrum containing the signal envelope from the plasma lipoproteins and the underlying GlycA and GlycB signals according to embodiments of the present invention.

FIG. 4A illustrates a chemical shift portion of the NMR spectrum between 2.080 and 1.845 ppm. FIG. 4A also illustrates both the calculated C signal and the measured (composite) signal envelope Cm from the allylic protons of the lipids in VLDL, LDL, and HDL, with underlying deconvolved GlycA and GlycB and other resonant peaks. GlycA can include contributions from 2-NAcGlc and 2-NAcGal methyl groups. GlycB includes signal from the N-acetyl methyl groups on the sialic acid moieties of glyeoproteins.

A defined mathematical deconvolution model can be used to measure the GlycA and/or GlycB. The "composite" or measured signal envelope Cm can be deconvolved to quantify the signal contributions of GlycA and GlycB and other contributing components such as lipoprotein subclass components. The deconvolution calculates signal amplitudes of the components contributing to the measured signal shapes and calculates the sum of the components. A close match between the calculated signal C and the measured signal Cm indicates the deconvolution successfully modeled the components that make up the NMR signal.

The peak region of the GlycA region GA and the peak of the GlycB region GB are shown by the peaks centered at 2.04 ppm and 2.00 ppm (at about 47 deg C. sample temperature), respectively, underlying the composite (upper) envelope signal line Cm. In some embodiments, the peak regions for GlycA and GlycB can include adjacent smaller nearby signals in the deconvolution model to account for GlycA and GlycB signals of slightly different frequency.

The protein signal Ps includes "humps" or peaks $P_{GA}$ and $P_{GB}$ that align with GA and GB, respectively. GlycA can be calculated using the difference between total plasma GlycA signal or "GA" as given by the total peak area of the plasma GlycA signal and "$P_{GA}$", that portion of GlycA that may derive from the non-inflammatory glycoproteins in the protein (d>1.21 g/L) component of plasma. The deconvolution can be carried out to subtract out the (patient/subject) variable "clinically non-informative" part of the total NMR signal at the GA region to leave the more informative disease association measure of GlycA.

Stated differently, while not being bound to any particular theory, in some embodiments, the measured GlycA signal at 2.00 ppm can be referred to as GA, the deconvolution can separate it into 3 parts: 1) the part contributed to by the protein (d>1.21 g/L) chosen to be largely devoid of inflammatory proteins, 2) the part contributed to by the non-inflammatory lipoproteins (d<1.21 g/L), and 3) the inflammatory glycoproteins (both lipoprotein and protein), the latter modeled by the overlapping Lorentzians (LGA) or other curve fit functions. The clinically informative GlycA from the deconvolution can be defined as GA minus $P_{GA}$ and minus the non-inflammatory lipoprotein components=LGA. GlycB can be determined in a similar manner using the GB minus $P_{GB}$ signal contribution minus the non-inflammatory lipoprotein components.

The lineshape deconvolution can be achieved with a non-negative least squares fitting program (Lawson, C T, Hanson R J, Solving Least Squares Problems, Englewood Cliffs, N.J., Prentice-Hall, 1974). This avoids the use of negative concentrations which can lead to error especially in low signal to noise spectra. Mathematically, a suitable lineshape analysis is described in detail for lipoproteins in the paper by Otvos, J D, Jeyarajah, E J and Bennett, D W, Clin Chem, 37, 377, 1991. A synthetic baseline correction function may also be used to account for baseline offsets from residual protein components. This can take the form of a quadratic or other polynomial function. Weighting factors are determined and the fit can be optimized by minimizing the root mean squared deviation between the experimental and calculated spectrum. See, e.g., U.S. Pat. Nos. 4,933,844 and 6,617,167 for a description of deconvolving composite NMR spectra to measure subclasses of lipoproteins, the contents of which are hereby incorporated by reference as if recited in full herein. See also, U.S. Pat. No. 7,243,030 for a description of a protocol to deconvolve chemical constituents with overlapping signal contribution, the contents of which are hereby incorporated by reference as if recited in full herein.

Figure 4B:
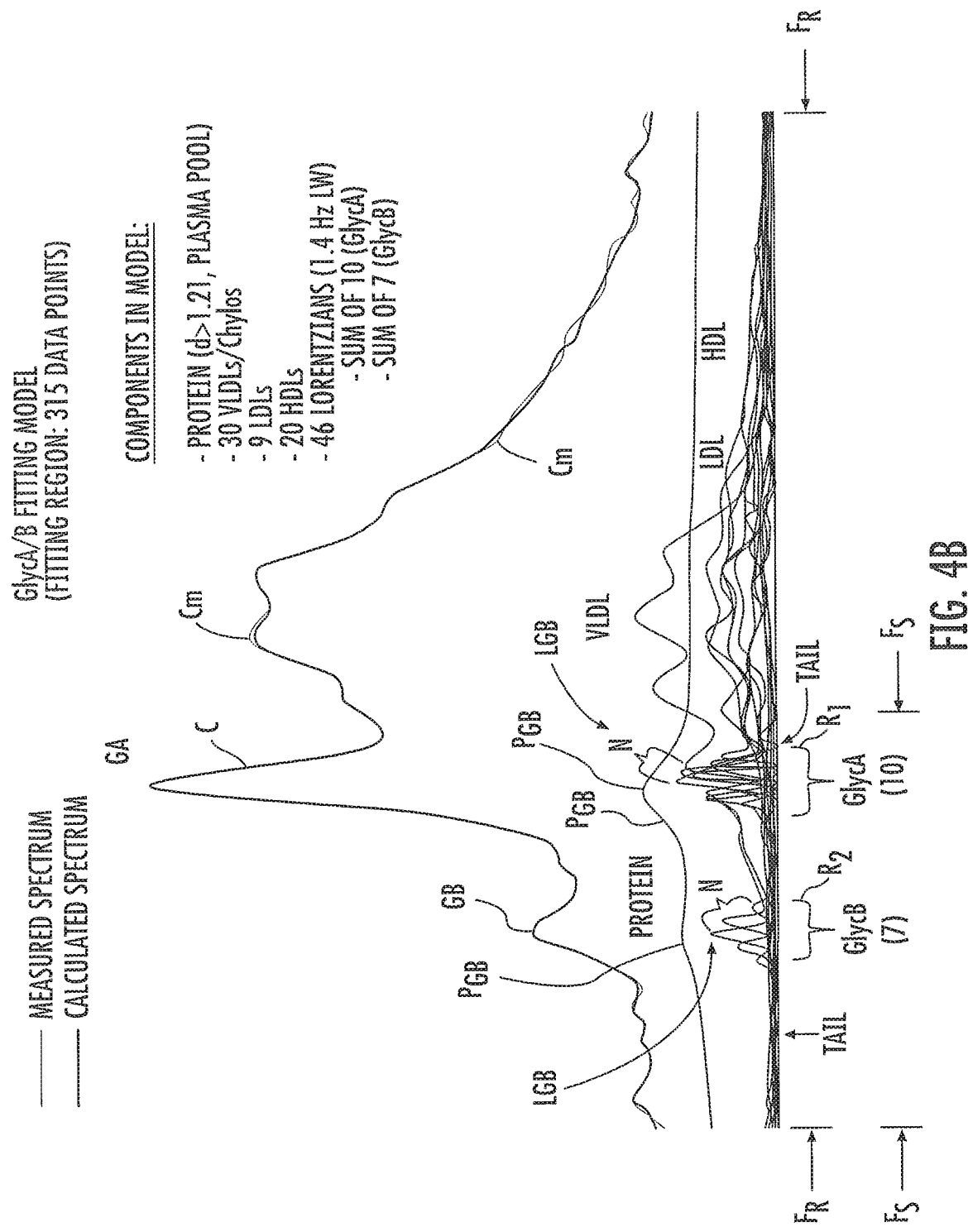
FIGS. 4B and 4C are graphs of the NMR spectral region shown in FIG. 4A illustrating deconvolution models to yield NMR signal for measurement of GlycA and GlycB according to embodiments of the present invention.
Figure 4C:
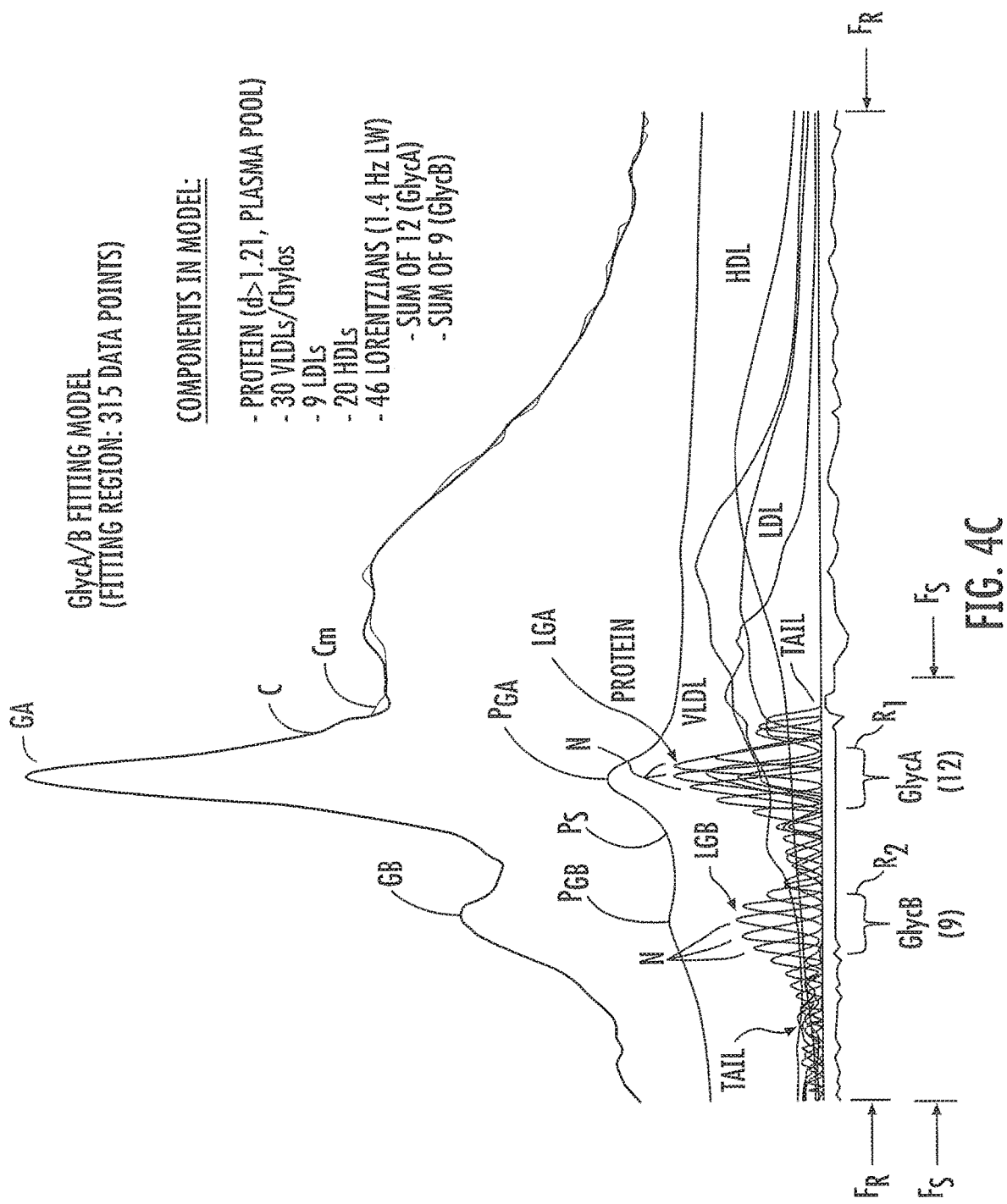

FIGS. 4B and 4C illustrate the composite (measured) signal "Cm" of the NMR spectra of FIG. 4A with a fitting region $F_R$ corresponding to the NMR spectrum between 2.080 and 1,845 ppm. The fitting region $F_R$ typically comprises 315 data points but more or less may be used, such as between about 200-400 data points, for example. The GlycA quantification model includes VLDL/chylos components, LDL components, and HDL components. Table 1 shows various TRLs that may be quantified in a deconvolution model according to embodiments of the present invention.

TABLE 1

Characteristics of Triglyceride Rich Lipoprotein Subclasses Measured by NMR LipoProfile ® Analysis

| Subclass | TRL Subclass Components | NMR Chemical Shift (ppm) | Estimated Diameter (nm) |
| --- | --- | --- | --- |
| Chylomicrons | C-260 | 0.8477 | 260 |
| Chylomicrons | C-250 | 0.8470 | 250 |
| Chylomicrons | C-240 | 0.8464 | 240 |
| Chylomicrons | C-225 | 0.8457 | 275 |
| Chylomicrons | C-200 | 0.8443 | 200 |
| Chylomicrons | C-190 | 0.8440 | 190 |
| Chylomicrons | C-185 | 0.8436 | 185 |
| Chylomicrons | C-180 | 0.8429 | 180 |
| Chylomicrons | C-175 | 0.8422 | 175 |
| Chylomicrons | C-170 | 0.8416 | 170 |
| TRL V6 | V6-140 | 0.8402 | 140 |
| TRL V6 | V6-120 | 0.8388 | 120 |
| TRL V6 | V6-100 | 0.8374 | 100 |
| TRL V5 | V5-80 | 0.8361 | 80 |
| TRL V5 | V5-70 | 0.8347 | 70 |
| TRL V5 | V5-60 | 0.8333 | 60 |

The term "TRL V6" refers to TRL (triglyceride rich lipoprotein) particles or sub-fractions having a diameter between about 90 nm up to as much as about 170 nm, more typically having diameters between about 100-140 nm. The term "TRL V6" can also be defined with respect to the lipid methyl group NMR signal chemical shifts (ppm) corresponding to the estimated diameters as provided in Table 1 above.

The term "TRL V5" refers to large TRL particles having a diameter of between about 60 nm and about 80 nm (see Table 1 above for the associated NMR chemical shifts).

The terms "chylomicron" and "chylos" refer to very large TRL particles having diameters that are larger than TRL V6. As such chylomicrons reters to TRL particles or sub-fractions having a diameter between from about 170 nm up to about 260 nm see Table 1 below for their associated NMR chemical shifts). There is not a clear demarcation between TRL V5 and TRL V6 nor between TRL V6 and chylomicrons, such that there is a distribution of particle sizes for each subgroup that overlaps in the range between about 80-90 nm for TRL V5-6 and between about 140-170 nm for TRL V6 and chylomicrons.

When the TRLs are quantified, the concentrations in particle concentration units (nmol/L) or triglyceride concentration units (mg/dL) can be expressed. Thus, for each of the different definitions of "large VLDL", either the particle concentrations or triglyceride concentrations could be used in the DRI model. Without wishing to be bound to any particular theory based on linear regression analysis, the triglyceride concentration units may yield marginally better diabetes risk prediction.

FIGS. 5A-5B) illustrate spectral overlaps from triglyceride rich lipoproteins as the TG (triglyceride) values increase which can be challenging to reliably deconvolve in a manner that provides precise and reliable GlycA and GlycB measurements.

The model provides sufficient HDL, LDL and VLDL/chylos components to be able to provide a good fit of the experimental signal as indicated by a close match between calculated signal C and experimental or measured composite signal Cm. Typically, the model will have more of the closely spaced VLDL/chylos components than either LDL or HDL components as these TRL contribute more signal to the left side of the spectrum. The model can include 20-50 VLDL/chylos components, typically about 25, 26, 27, 28, 29, 30, 31, 32, 33, 34, 35, 36, 37, 38, 39 or 40. In a preferred embodiment, the model includes 30 VLDL/chylos components.

The model can include a plurality "N" of (typically overlapping) curve fit components N that populate a sub-region Fs of the fitting region $F_R$ that extends from a few data points (e.g., about 10 or less) to the right of the GlycA measurement region $R_1$ (e.g., starting at about 1.9 ppm or higher) to at least a few data points to the left of the GlycB region $R_2$ (and can extend to the end of the fitting region $F_R$ to 2.080 ppm). Each component N, in this embodiment, can be a Lorentzian-shaped signal with a linewidth about 1.4 Hz. Also, in particular embodiments, each data point can be about 0.275 Hz apart as determined by digital resolution of the spectrum. The tail portion of the region Fs on the left side may include more (Lorentzian) components than the tail portion on the right side. The number of components N in the region Fs n can be about 46 (e.g., about 46 Lorcnztians) but more or less components "N" can be used. For example, the region Fs can include, but is not limited to, between 30-70 Lorenztians, or n=30, 35, 36, 37, 38, 39, 40, 41, 42, 43, 44, 45, 46, 47, 48, 49, 50, 51, 52, 53, 54, 55, 56, 57, 58, 59, or 60. The curves N are typically Lorentzian functions with line widths at half-height of between 2-10 data points (0.55-2.75 Hz at 400 MHz), more typically between 4-6 data points, and are offset from each other by a defined amount, such as, for example, 2 data points (0.55 Hz).

The GlycA and GlycB Lorentzians (or other curve fitting components N) can have the same or different numbers of data points. The GlycB Lorentzians N can have the same, less or more data points than the GlycA Lorentzians N. The Lorentzian fit components "N" can have peak line widths (LW) of about 1.4 Hz (at half height). However, other LWs can be used including, but not limited to, 1.1, 1.2, 1.3, 1.5 and the like.

GlycA can be calculated using a defined subset of the number of curve fit components N that fill the entire region $R_1$ and GlycB can be calculated using a suitable number of curve fit (e.g., Lorentzian fit) components N that fill the entire region $R_2$. The region $R_1$ can be between 5-6 Hz. The GlycB region $R_2$ can be 7-8 Hz. Optionally, the GlycA components N can be offset by 2 data points while the GlycB components N can be offset by 4 data points.

GlycA can be calculated using a sum of adjacent Lorentzian components N, typically between 9-15, such as 9, 10, 11, 12, 13, 14 and 15 components. GlycB can be the sum of adjacent Lorentzian fit components N, with the same, more, or less, typically less, than that used for GlycA measurements, such as between about 5-10 components N, typically about 7, about 8 or about 9 components. The Lorentzians between $R_1$ and $R_2$ are not included in the quantified measurement of either GlycA or GlycB. FIG. 4B illustrates the sum of 7 adjacent Lorentzians used to calculate the GlycB measurement and the sum of 10 (more narrow) Lorentzians can be used to calculate the GlycA measurements. FIG. 4C illustrates the sum of 9 adjacent Lorentzians used to calculate the GlycB measurement and the sum of 12 (more closely spaced) Lorentzians can be used to calculate the GlycA measurements.

The number of HDL, LDL and VLDL components may vary. As shown, the HDL components can be 20 HDL components (spanning the range of HDL subclass diameters), but more or less can be used, e.g., between about 10-26. As shown, the number of LDL components is 9 components (representing different LDL diameters), but more or less can be used, e.g., between about 5-20, As shown, the number of VLDLs/Chylos components is 30, but more or less can be used, e.g., 25-60 of different size ranges.

To be clear, while a preferred embodiment describes the curve fit components as Lorentzian fit components, other fitting components may be used including, but not limited to, experimental N-acetyl methyl group signals or Gaussian lineshape functions. Thus, any suitable curve fit function can be used.

Figures 6A, 6B, 6C, 6D:
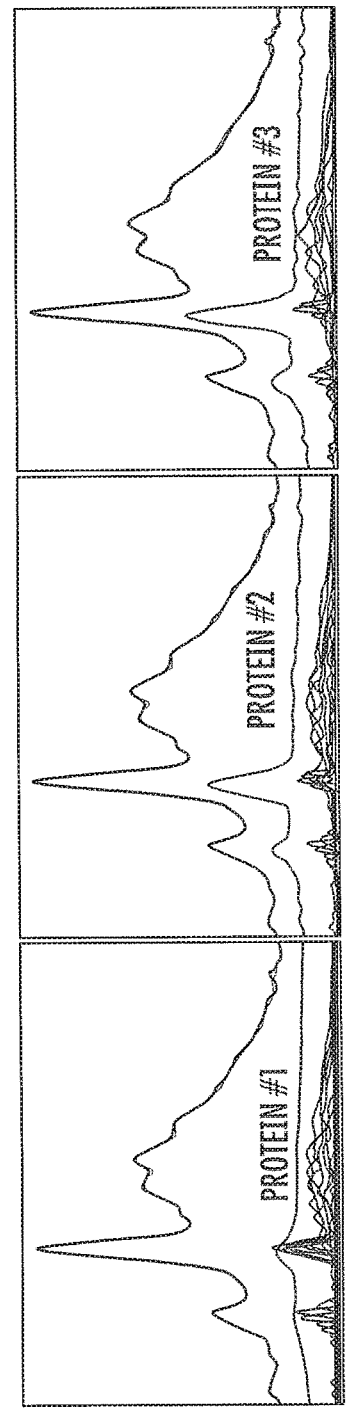
FIG. 6A is a table of different measures of GlycA concentration, depending on a protein component used in the deconvolution (e.g., "fitting") model.
FIGS. 6B-6D illustrate the GlycA and GlycB "fits" (deconvolution) of the same plasma sample using deconvolution models with different protein components (#1-#3 in the table in FIG. 6A) according to embodiments of the present invention.

FIG. 6A is a table of different protein components (Protein 1, Protein 2 and Protein 3) that, when used in the Glyc deconvolution model, yields different GlycA concentrations and different GlycA associations with CHD events and All-Cause Death in MESA. FIGS. 6B, 6C and 6D) illustrate the respective protein signal Ps in the deconvolved spectrum and the differences they exhibit in the amplitudes of the signals in the GlycA and GlycB peak regions. To optimize the calculated GlycA and/or GlycB measurement, in some embodiments, the deconvolution model includes a defined protein signal component as discussed above. This protein signal component Ps is for protein other than lipoproteins, e.g., other than HDL, LDL, VLDL/chylos, e.g., and may be associated with the >1.21 g/L density fraction of plasma obtained by ultracentrifugation (which includes albumin and other non-lipoprotein proteins in plasma).

The table in FIG. 6A represents associations of GlycA with CHD events (n=289) and All Cause Death (n=346) that are from logistic regression analysis adjusted for age, gender, race, smoking, systolic blood pressure, hypertension medications, body mass index, diabetes, LDL-P and HDL-P. The likelihood ration $\chi^2$ statistic gives a quantitative measure of the extent to which GlycA improves prediction of outcomes when added to the 10 covariates in the regression model.

This signal component "Ps" is shown in FIGS. 4A-4C. Surprisingly, although this protein signal Ps does include a peak ($P_{GA}$, $P_{GB}$, respectively) aligned with the peak at the chemical shift for both GlycA and GlycB, eliminating this portion of the protein NMR signal from the deconvolution model (by, for example, digital manipulation or signal processing) was found to make the calculated GlycA and GlycB measurements relatively less clinically informative (weaker disease associations). At the other extreme, including in the deconvolution model a protein component with a relatively large signal at the GlycA and GlycB positions results in lower GlycA and GlycB concentrations that are also less clinically informative, as shown for Protein #2 and Protein #3 in FIGS. 6C and 6D). Thus, by selecting an appropriate protein component with an intermediate signal amplitude at the GlycA and GlycB positions, such as Protein #1 in FIG. 6B, the deconvolution model may be "tuned" to produce GlycA and GlycB concentrations that are improved and/or optimized with respect to their clinical associations with inflammation and related disease states.

Thus, in some embodiments, it is contemplated that the GlycA measurement will provide a better clinical indicator if it does not include the lipoprotein signal (accounted for in the deconvolution model with the VLDL/chylo, LDL and HDL components) and if it includes only a portion of the remaining NMR signal, e.g., it does not include all other NMR protein signal at the GlycA peak region. This subset of the NMR signal at the GlycA peak region may be more reflective of inflammatory protein activity, e.g., N-acetyl methyl signals from glycosylated acute phase proteins.

Figure 7A:
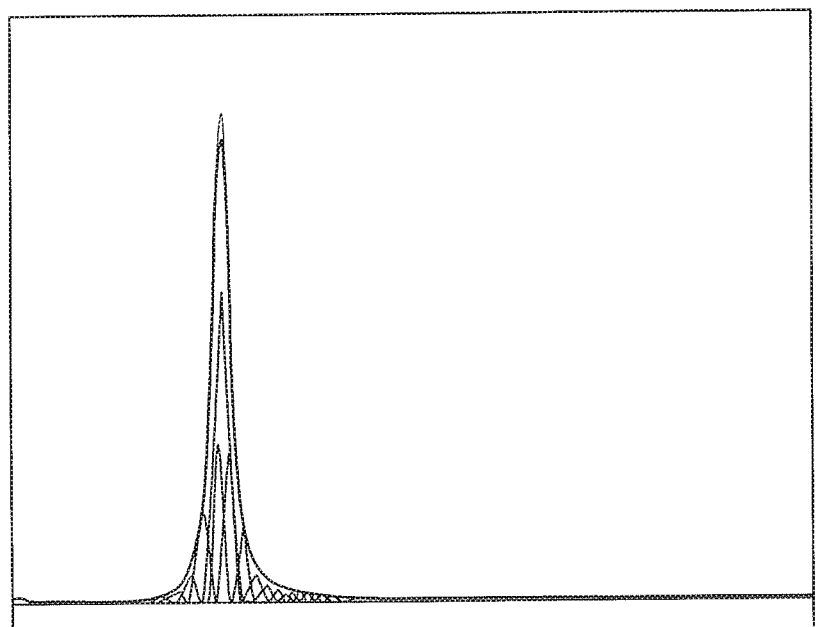
FIG. 7A is a schematic screen shot of the deconvolution of a 10 μmmol/L reference sample of N-acetylglucosamine, used to generate a conversion factor relating GlycA and GlycB signal areas to glycoprotein N-acetyl methyl group concentrations according to embodiments of the present invention.

FIG. 7A is a screen shot of the deconvolution of a 10 mmol/L reference standard sample of N-acetylglucosamine, from which a conversion factor of 17.8 was determined to transform signal area concentrations of GlycA and GlycB to µmol/L glycoprotein N-acetyl methyl group concentrations. In some embodiments, according to MESA subjects, first to fourth quartile (mean) levels of GlycA (FIG. 14) can be: Q1: 21.6*17.8, Q2: 25.8*17.8, Q3: 29.3*17.8 and Q4: 35.3*17.8.

GlycA measurement precision using the model shown in FIG. 4B was shown to be good. A within-run (5 pools from 2009) analysis of lowest GlycA=40.5 (CV=2.47%) and highest GlycA=58.4 (CV=1.6%). Within-lab results from 13 pools from 2010 and 2011 had a lowest GlycA=25.6 (CV=4.08%) and highest GlycA=69.1 (CV=1.87%). These concentrations are expressed as "arbitrary units" of NMR signal areas and can be multiplied by 17.8 to convert them to µmol/L N-acetyl methyl group concentrations.

FIG. 7B is a table of components that may be used in a GlycA/B deconvolution model. Metabolite A is one component that can be measured in a GlycA/B deconvolution model and may be used clinically. As illustrated in FIGS. 7C and 7D, metabolite A can be present in a spectrum as a singlet peak and is typically present in a sample at low concentrations (FIG. 7C), but a high concentration of metabolite A may be present in a sample (FIG. 7D). A plurality of curve fitting functions for the metabolite A peak region can be used to quantitatively evaluate a level of metabolite A and/or to deconvolve the NMR spectrum for quantification of GlycA and/or GlycB, for example.

The deconvolving model components shown in FIG. 7B list a plurality of curve fit functions Glyc1-Glyc46 that can be applied to a fitting region that includes the GlycA peak region and extends to a GlycB peak region (typically with between about 40-50 curve fit functions, shown as with 46, but less or more such curve fit functions may be used, e.g., between 30-100). As discussed above, the GlycA measurement can be carried out by summing values of a defined first subset of the curve fit functions, values associated with all or some of the Glyc1-Glyc 26 components, for example. The GlycB measurement can be carried out by summing values of a second (typically smaller) defined subset of the curve fit functions, such as some or all components between Glyc27 and Glyc 46, for example.

Figure 8A:
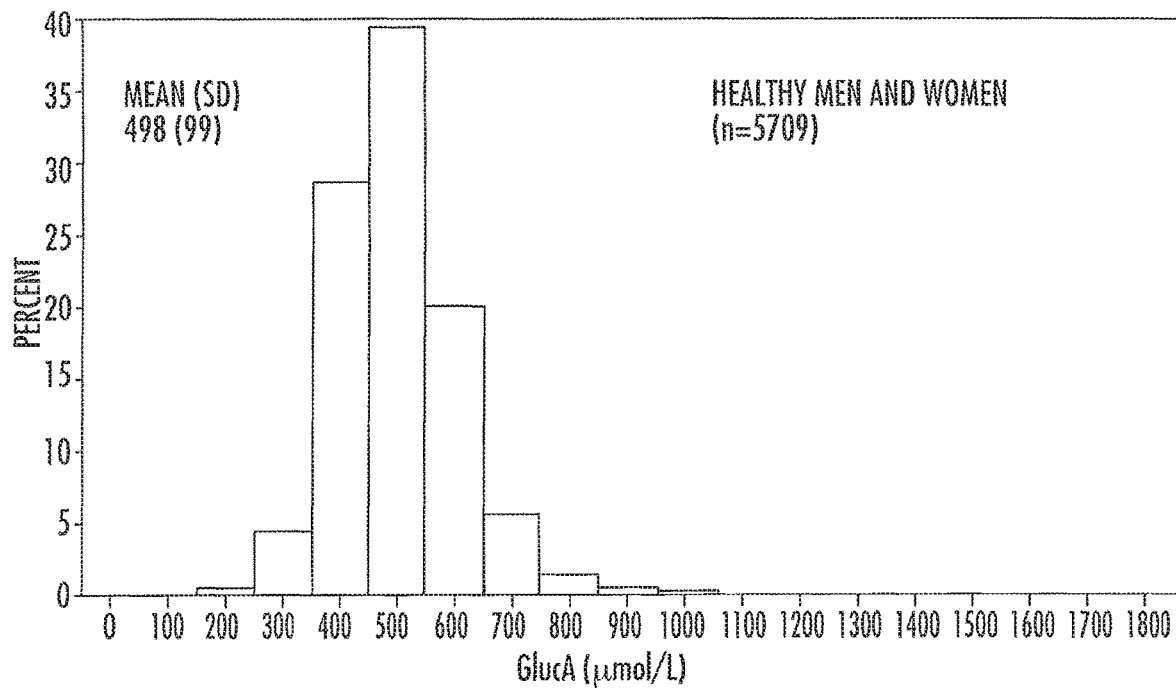
FIGS. 8A and 8B are graphs of distributions of NMR-measured GlycA levels (in methyl group concentration units) of two different populations.
Figure 8B:
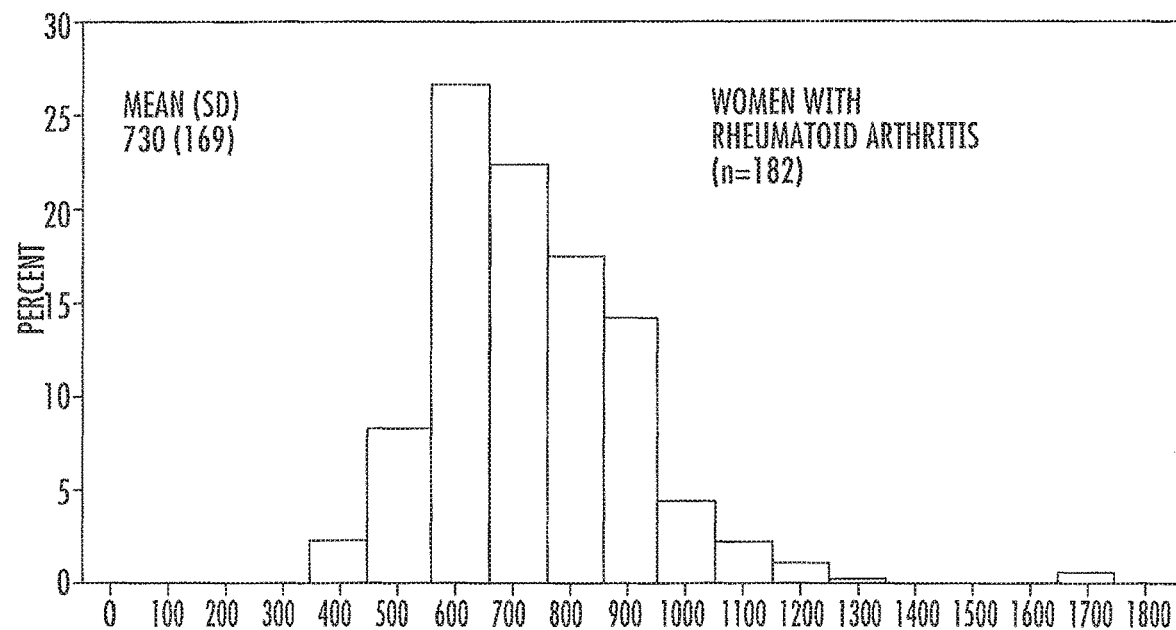

FIGS. 8A and 8B are histogram graphs of NMR-measured GlycA values from two different study populations. FIG. 8B provides NMR measures of GlycA for 182 women with rheumatoid arthritis (RA), a known chronic inflammatory disease, while FIG. 8A gives values from the MESA population of healthy men and women without known inflammatory disease.

It is believed that the measured amplitude of the GlycA signal in any one sample may have the advantage of providing a more stable and "time-integrated" measure of the patient's inflammation state than is provided by measurements of hs-CRP or other individual inflammatory proteins.

FIG. 9 is a chart of prospective associations of hs-CRP and NMR measured GlycA and Valine levels with various exemplary disease outcomes based on MESA data (n≈5680). The chart was generated from logistic regression analyses adjusted for age, gender, race, smoking, systolic blood pressure, hypertension medications, body mass index, diabetes, LDL-P and HDL-P. The likelihood ratio statistic $\chi 2$ gives a quantitative measure of the extent to which the indicated variable improves disease prediction when added to the 10 covariates in the regression model. The analyses used GlycA measurement values from the deconvolution model shown in FIG. 4B. The right side column shows that GlycA and Valine are additive in their associations with disease when they both have significant associations examined separately.

Figure 10A:
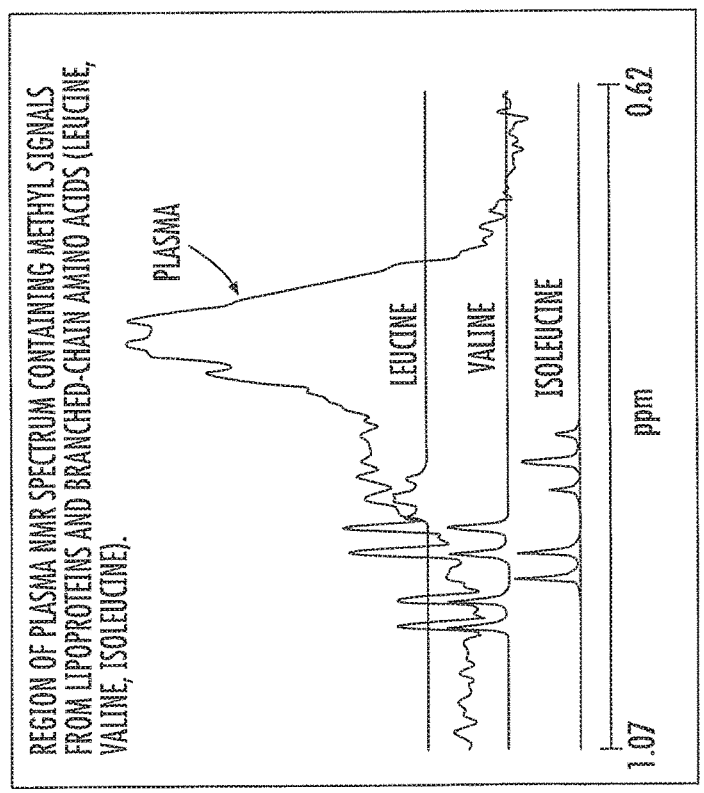
FIG. 10A is a region of the plasma NMR spectrum containing methyl signals from lipoproteins and branched-chain amino acids.
Figure 10B:
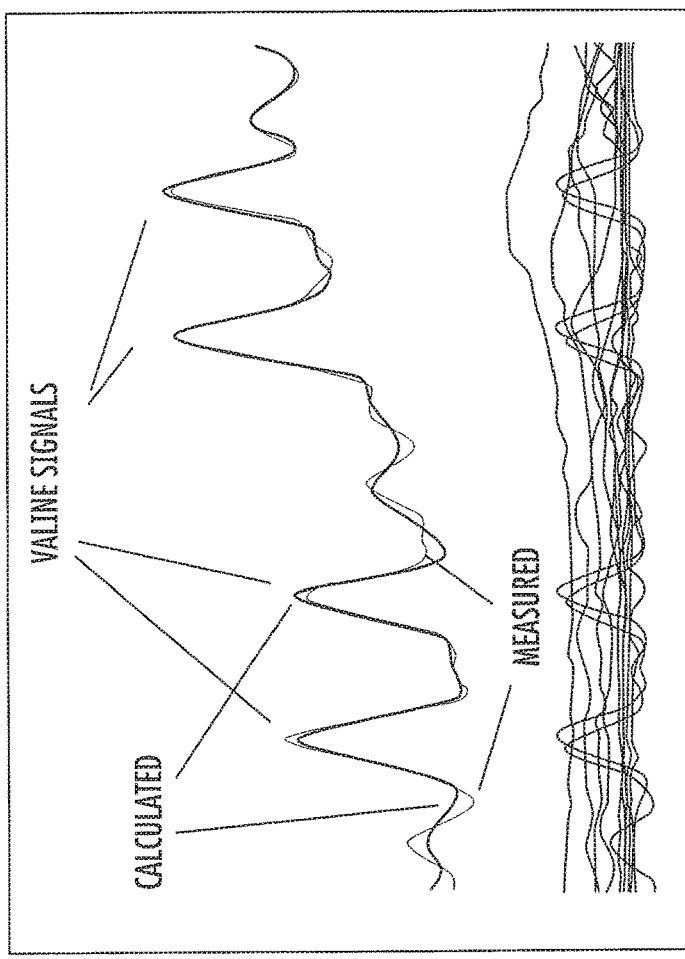
FIG. 10B is an example of a fitting function/deconvolution model that uses four valine signals (two doublets) to calculate NMR measures of valine according to embodiments of the present invention.

In some embodiments, the NMR measurement can include both GlycA and Valine, and each can be provided in a patient report for clinical consideration. FIG. 10A is a graph showing a region of plasma NMR spectrum containing methyl signals from lipoproteins and branched-chain amino acids (leucine, valine and isoleucine). FIG. 10B is an example of a deconvolved signal with a quartet of valine signals identified to generate a calculated C and measured Cm spectrum of the valine signals with two doublets of valine NMR signal (between about 0.90-1.07) that can be used to measure valine.

It is contemplated that NMR measurements of both GlycA and Valine of a single (blood/plasma) in vitro biosample can provide important clinical information and/or further improve a prediction or evaluation of a patient or subject's risk of having a clinical disease state or being at increased risk for same and/or to evaluate risk of all-cause death.

As is generally accepted, HDL-cholesterol and/or LDL-cholesterol levels provided by conventional lipid panels fail to sufficiently differentiate populations with and without elevated risk for CHD/CAD. As is known to those of skill in the art, the Framingham study proposed a relatively lengthy risk model that considers many factors such as age, gender, smoking habits, as well as cholesterol values. The research conducted in the Framingham Offspring Study also defined normative and at-risk population values from subjects in the study. See Wilson et al., *Impact of National Guidelines for Cholesterol Risk Factor Screening. The Framingham Offspring Study*, JAMA, 1989; 262: 4144.

It is contemplated that inflammation is a separate contributor to heart attack risk. While not wishing to be bound to any particular theory of metabolic activity and risk, it is contemplated that, for example, if a patient has a stable form of atherosclerosis (the plaque or associated protein is stable within an arterial wall, for example), then the risk of a cardiac event may be less than if that same patient also exhibits inflammation, which may weaken a protein cover that makes the plaque susceptible to rupture, and hence present an increased risk of CHD and/or myocardial infarction (MI).

According to particular embodiments, NMR measures of GlycA, alone or with other defined analytes (e.g., one or more of GlycB, LDL-P, Mg or Valine), can provide a more robust and more readily measured health/death risk assessment over hs-CRP, the latter of which is present in a respective patient in vitro sample in very low levels.

As noted above, FIG. 7A illustrates a conversion factor that can be used to calculate measurements of GlycA. The GlycA measurement can also be a unit less parameter as assessed by NMR by calculating an area under a peak region at a defined peak in NMR spectra. In any event, measures of GlycA with respect to a known population (such as MESA) can be used to define the level or risk for certain subgroups, e.g., those having values within the upper half of a defined range, including values in the third and fourth quartiles, or the upper 3-5 quintiles and the like.

FIG. 8A illustrates a distribution of GlycA values for subjects from MESA. Bell et al., Assignment of resonances for 'acute-phase' glycoproteins in high resolution proton NMR spectra of human blood plasma, FEBS Letters, Vol. 215, No. 2, pp. 311-315 (1987) proposed that measurement of acute-phase reactive plasma glycoproteins could be of considerable value in the detection, prognosis and therapeutic monitoring of patients with tissue damage and compared "normal" levels with patients having melanoma, rheumatoid arthritis, and monoclonal gammopathy. The contents of this reference are hereby incorporated by reference as if recited in full herein. Despite the foregoing, and the many years since the publication of this research, the inventors of the instant patent application have unexpectedly found that despite the non-specific nature of the general inflammation information provided by acute phase reactive plasma glycoproteins, increased levels of GlycA can be a robust biomarker for CHD risk, stronger than hs-CRP.

FIG. 11 is a Table of mean values of various characteristics of MESA subjects within each of four quartiles of NMR measured GlycA. The mean GlycA level of those in the 3rd quartile is 29.3. This table shows that people with higher GlycA levels have characteristics associated with higher inflammation (more smoking, hypertension, hs-CRP, etc). NMR signal area units can be called "arbitrary" units. The GlycA levels in this table are in these "arbitrary units" that may be converted to methyl group concentration units (μmol/L) by multiplying by 17.8.

FIG. 12 is a chart of different models used to predict CHD events in MESA N=5607 with n=289 CHD events from Cox logistic regression models adjusted for age, sex, ethnicity, smoking, systolic blood pressure (SBP), hypertension medication treatment (HTNrx), BMI (body mass index), diabetes LDL-P and HDL-P status. The model $\chi 2$ statistic provides a quantitative measure of the extent to Which the added variable in the model improves CHD risk prediction. The parameter/marker $\chi 2$ statistic and corresponding "p" value quantify the magnitude and statistical significance of the improved prediction given by the inflammation marker to the model. Notably, as shown in FIG. 12, GlycA has a 10.4 $\chi^2$ value, more than fibrinogen and hs-CRP (indeed, hs-CRP had the lowest of the three parameters, with a marker $\chi 2$ of 1.8).

FIG. 13 is a table of associations with All-Cause Death in MESA N=5607, 345 deaths. The Cox models were adjusted for age, sex, ethnicity, smoking, SPB, hypertension medication, BMI and diabetes. HDL-P, GlycA and a model with both HDL-P and GlycA parameters in the base model showed improved risk prediction.

Figure 14:
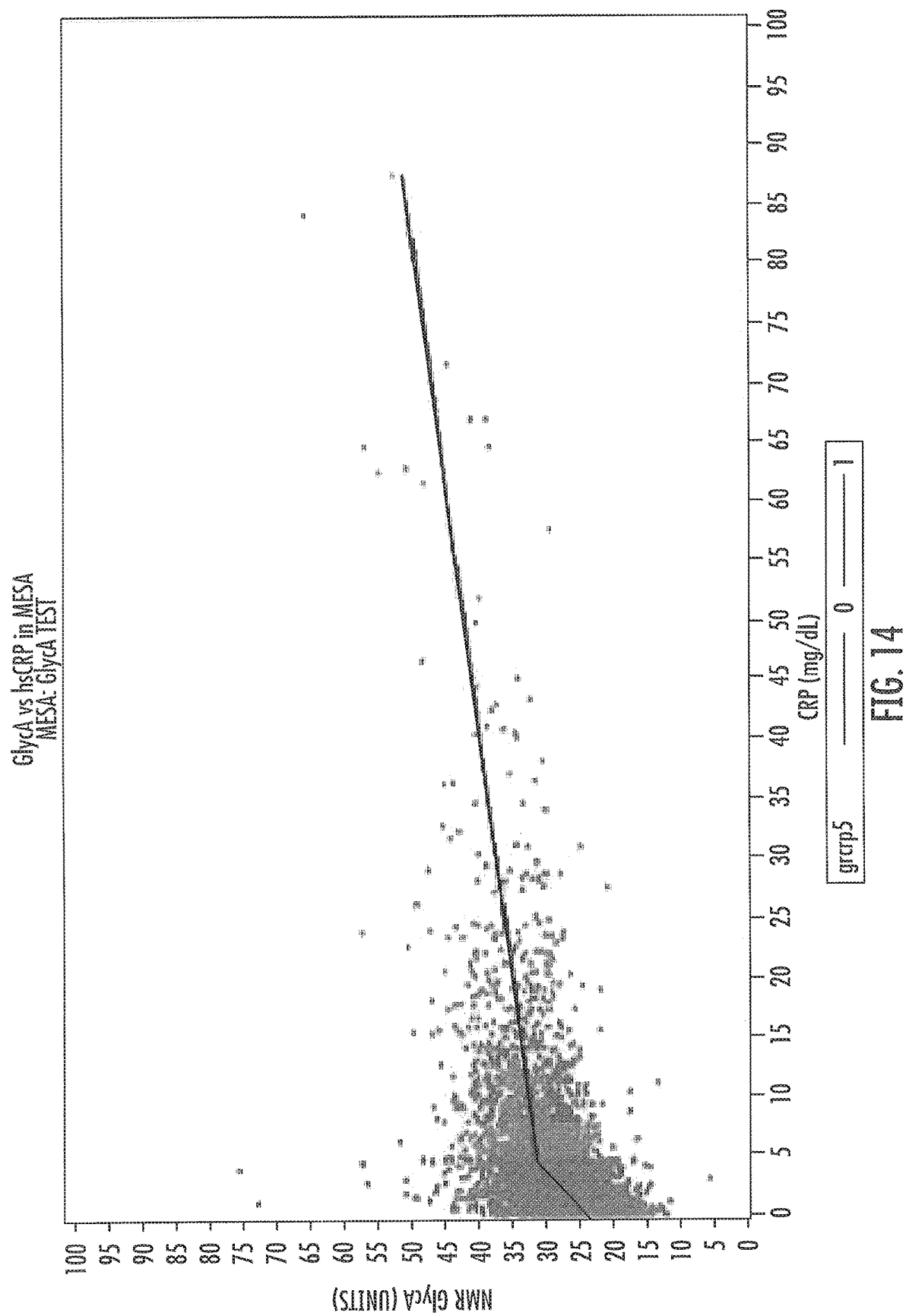
FIG. 14 is a graph of NMR measured GlycA (NMR signal area units versus CRP (mg/dL) showing linear regressions for hsCRP values <5 and ≥5 mg/dL based on MESA data according to embodiments of the present invention.

FIG. 14 is a graph of NMR GlycA (signal area units) versus hs-CRP >5 mg/dL based on MESA data. Linear regressions are shown for 2 hs-CRP ranges, 0-5 and >5 mg/dL. The steeper slope of the regression for lower values of CRP shows that GlycA is reflective of chronic inflammation status, but is less reflective of differences in acute inflammation that pertain to those with CRP levels >5 mg/dL.

Figure 15A:
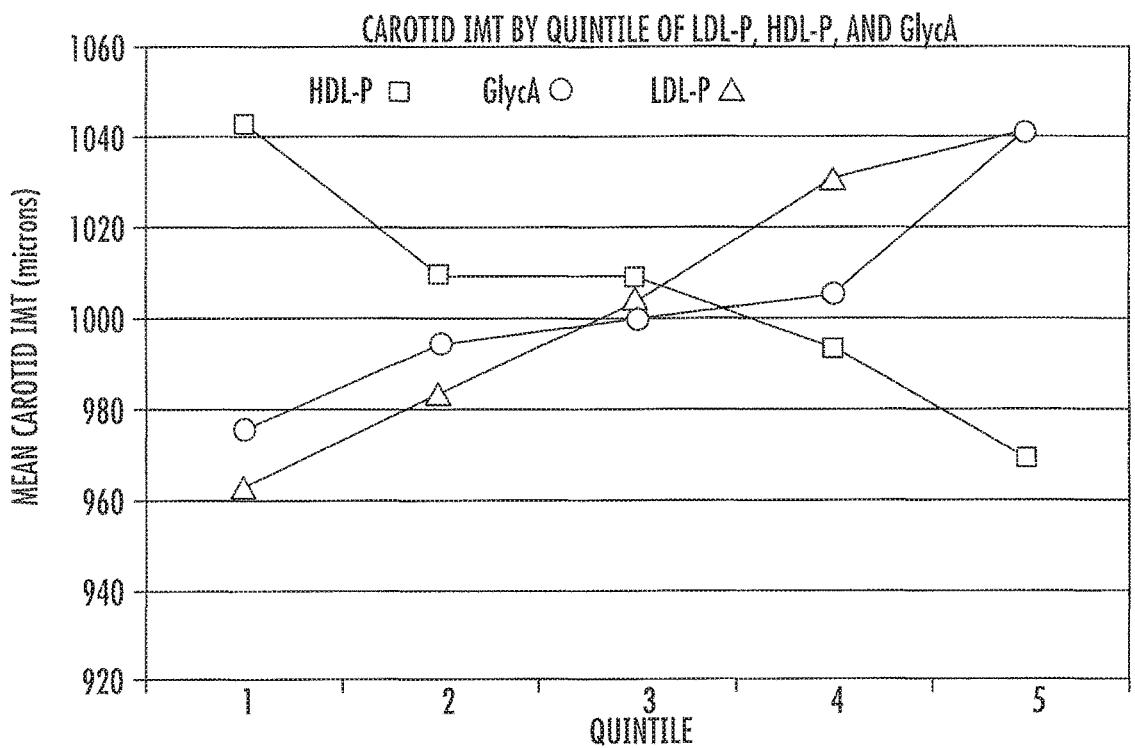
FIG. 15A is a graph of mean carotid IMT (microns) by quintile of LDL-P, HDL-P and GlycA according to embodiments of the present invention.

FIG. 15A is a graph of mean carotid IMT (microns) by quintile of LDL-P, GlycA and HDL-P from linear regression models adjusted for age, sex, ethnicity, SBP, hypertension medication, diabetes, BMI and smoking from unpublished MESA data. Elevated levels of both LDL-P and GlycA are associated with greater carotid IMT values, reflecting greater atherosclerotic risk.

Figure 15B:
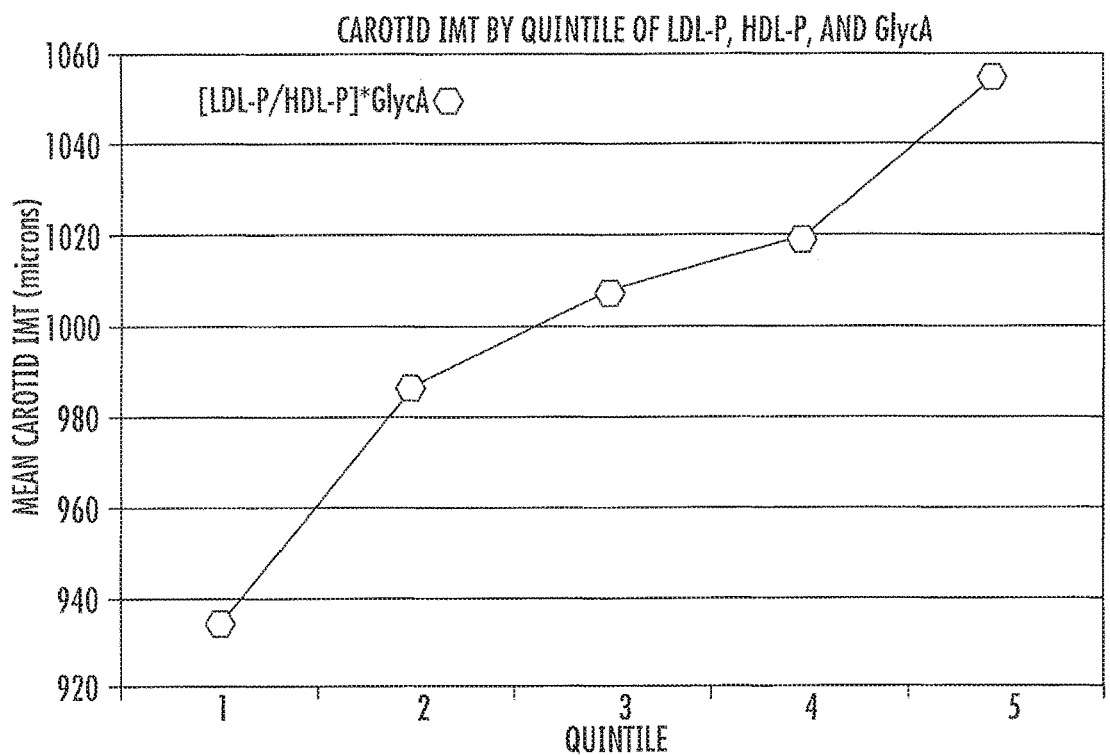
FIG. 15B is a graph of mean carotid IMT by quintile of a risk index comprised of LDL-P/HDL-P*GlycA according to embodiments of the present invention.

FIG. 15B is a graph of a single risk predictor of carotid IMT (related to CHD/CVD) based on the ratio of LDL-P/HDL-P multiplied by GlycA for carotid IMT (microns) versus quintile value based on unpublished data of MESA and the linear regression models discussed for FIG. 15A.

Embodiments of the invention contemplate that patient biosamples can be analyzed for increased levels of GlycA relative to a patient's own "baseline" and/or relative to a population standard or "norm" or other defined elevated level associated with an increased medical "risk". GlycA may also or alternatively be used as one parameter in a multiple parameter risk prediction model for a clinical disease state. The multiple parameter model for CHD can include lipoprotein parameters.

Figure 16:
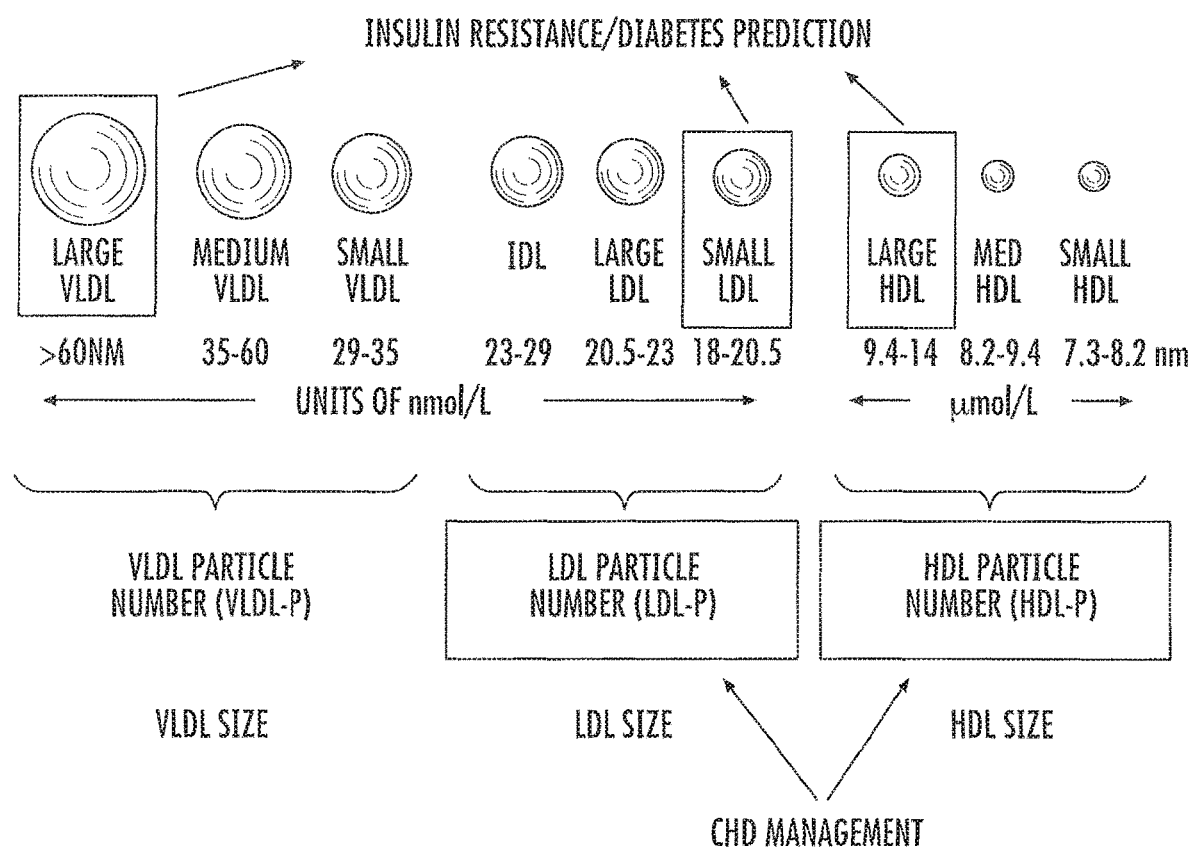
FIG. 16 is a schematic illustration of different lipoprotein parameters according to embodiments of the present invention.

FIG. 16 illustrates examples of lipoprotein subclass groupings, including those with concentrations that can be summed to determine HDL-P and LDL-P for CHD management/risk assessment according to some particular embodiments of the present invention. Embodiments of the invention classify lipoprotein particles into subclasses grouped by size ranges based on functional/metabolic relatedness as assessed by their correlations with lipid and metabolic variables. The evaluations can measure over 20 discrete subpopulations (sizes) of lipoprotein particles, typically between about 30-80 different size subpopulations (or even more). FIG. 16 also shows these discrete sub-populations can be grouped into defined subclasses, including three each for VLDL and HDL and two or three for LDL (if the former, with one of the three identified as IDL in the size range between large LDL and small VlDL). For the GlycA and/or GlycB measurement calculations, the discrete number of HDL and LDL groupings can be less than those used to quantitatively measure the lipoprotein subclasses.

HDL subclass particles typically range (on average) from between about 7 nm to about 15 nm, more typically about 7.3 nm to about 14 nm or 7.3-13.5 nm. The HDL-P concentration is the sum of the particle concentrations of the respective subpopulations of its HDL-subclasses, e.g., small HDL-P can include H1-H8 subpopulations. The large HDL subclasses can have a size range between 9.4-14 nm, typically between 9.7-13.5 nm. The HDL subclasses of different size can be quantified from the amplitudes of their spectroscopically distinct lipid methyl group NMR signals. See, Jeyarajah et al., *Lipoprotein particle analysis by nuclear magnetic resonance spectroscopy*, Clin Lab Med., 2006: 26: pp. 847-870, the contents of which are hereby incorporated by reference as if recited in full herein. The NMR derived HDL-P and LDL-P particle sizes noted herein typically refer to average measurements, but other size demarcations may be used.

As shown in FIG. 16, the small LDL particles can include particles whose sizes range from between about 18.0 to about 20.5 nm, typically between 19-20 nm. The large LDL particles can include particles ranging in diameter between about 20.5-23.0 nm. It is noted that the LDL subclasses of particles can be divided in other size ranges. For example, small may be between about 19.0-20.5 nm, intermediate may be between about 20.5-21.2 nm, and large may be between about 21.2-23 nm. In addition, intermediate-density lipoprotein particles ("IDL" or "IDL-P"), which range in diameter from approximately 23.0-29.0 nm, can be included among the particles defined as LDL. Thus, LDL particles can include sizes between 19.0-28 nm, for example. VLDL can have sizes between 29-100 nm or 29-160 nm, with large VLDL between 60 nm and 100 or 160 nm, respectively and chylos between 100-260 nm or 160 nm to 260 nm, respectively.

Figure 17:
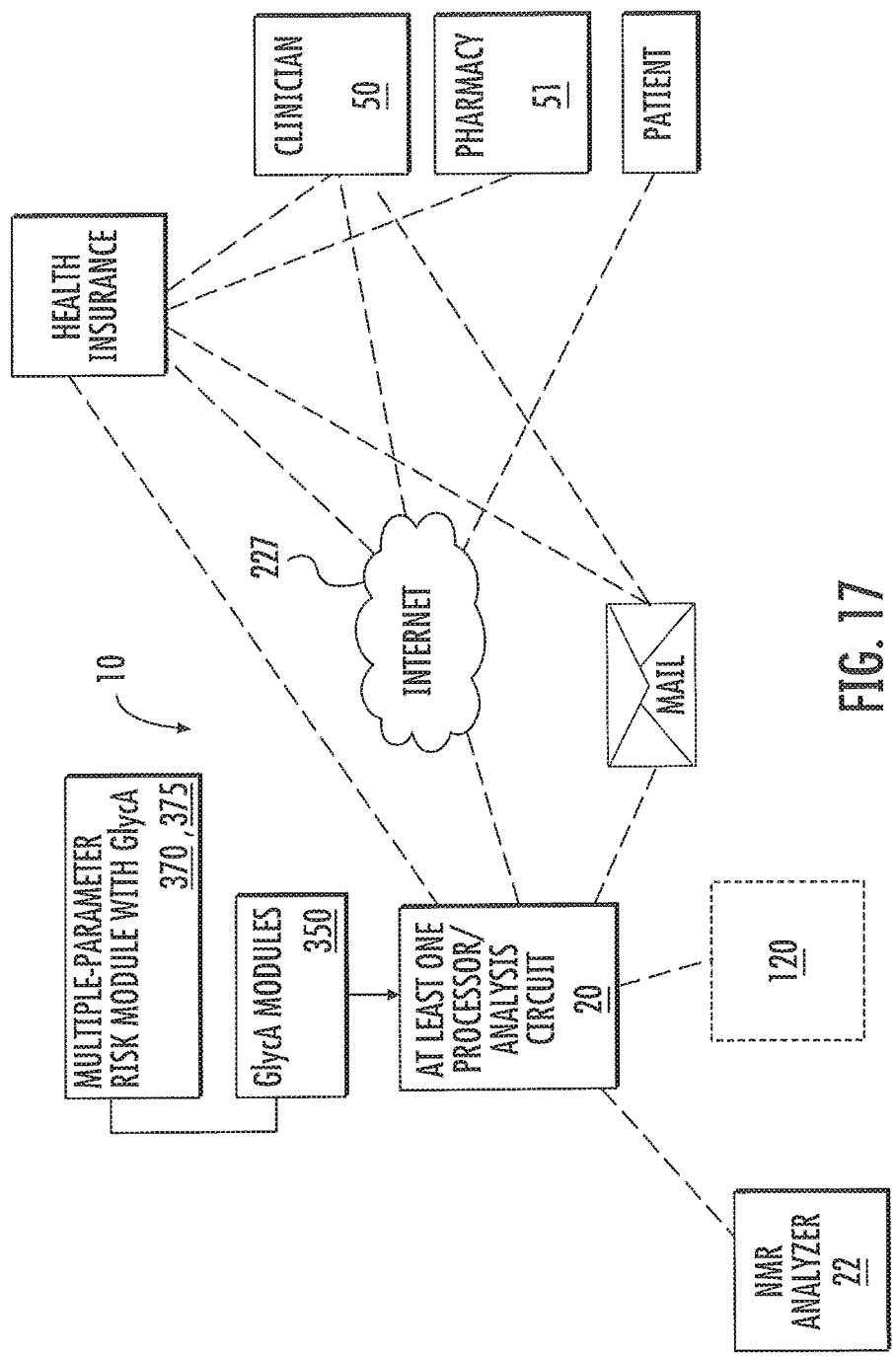
FIG. 17 is a schematic illustration of a system for analyzing clinical disease states and/or risk including a GlycA evaluation module and/or circuit using according to embodiments of the present invention.

Referring now to FIG. 17, it is contemplated that the GlycA and/or GlycB measurement analysis can be carried out using a system 10 with an NMR clinical analyzer 22 as described, for example, with respect to FIG. 18 below and/or in U.S. Pat. No. 8,013,602, the contents of which are hereby incorporated by reference as if recited in full herein. The analyzer 22 includes a spectrometer 22s and sample handler system.

The system 10 can include a GlycA analysis module and/or circuit 20 that can be onboard the analyzer 22 or at least partially remote from the analyzer 22. If the latter, the analysis module or circuit 20 can reside totally or partially on a server 150. The server 150 can be provided using cloud computing which includes the provision of computational resources on demand via a computer network. The resources can be embodied as various infrastructure services (e.g. computer, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers. Data transfer can be encrypted and can be done via the Internet using any appropriate firewalls to comply with industry or regulatory standards such as HIPAA. The term "HIPAA" refers to the United States laws defined by the Health Insurance Portability and Accountability Act. The patient data can include an accession number or identifier, gender, age and test data.

The results of the analysis can be transmitted via a computer network, such as the Internet, via email or the like to a patient, clinician site 50, to a health insurance agency 52 or a pharmacy 51. The results can be sent directly from the analysis site or may be sent indirectly. The results may be printed out and sent via conventional mail. This information can also be transmitted to pharmacies and/or medical insurance companies, or even patients that monitor for prescriptions or drug use that may result in an increase risk of an adverse event or to place a medical alert to prevent prescription of a contradicted pharmaceutical agent. The results can be sent to a patient via email to a "home" computer or to a pervasive computing device such as a smart phone or notepad and the like. The results can be as an email attachment of the overall report or as a text message alert, for example.

Figure 18:
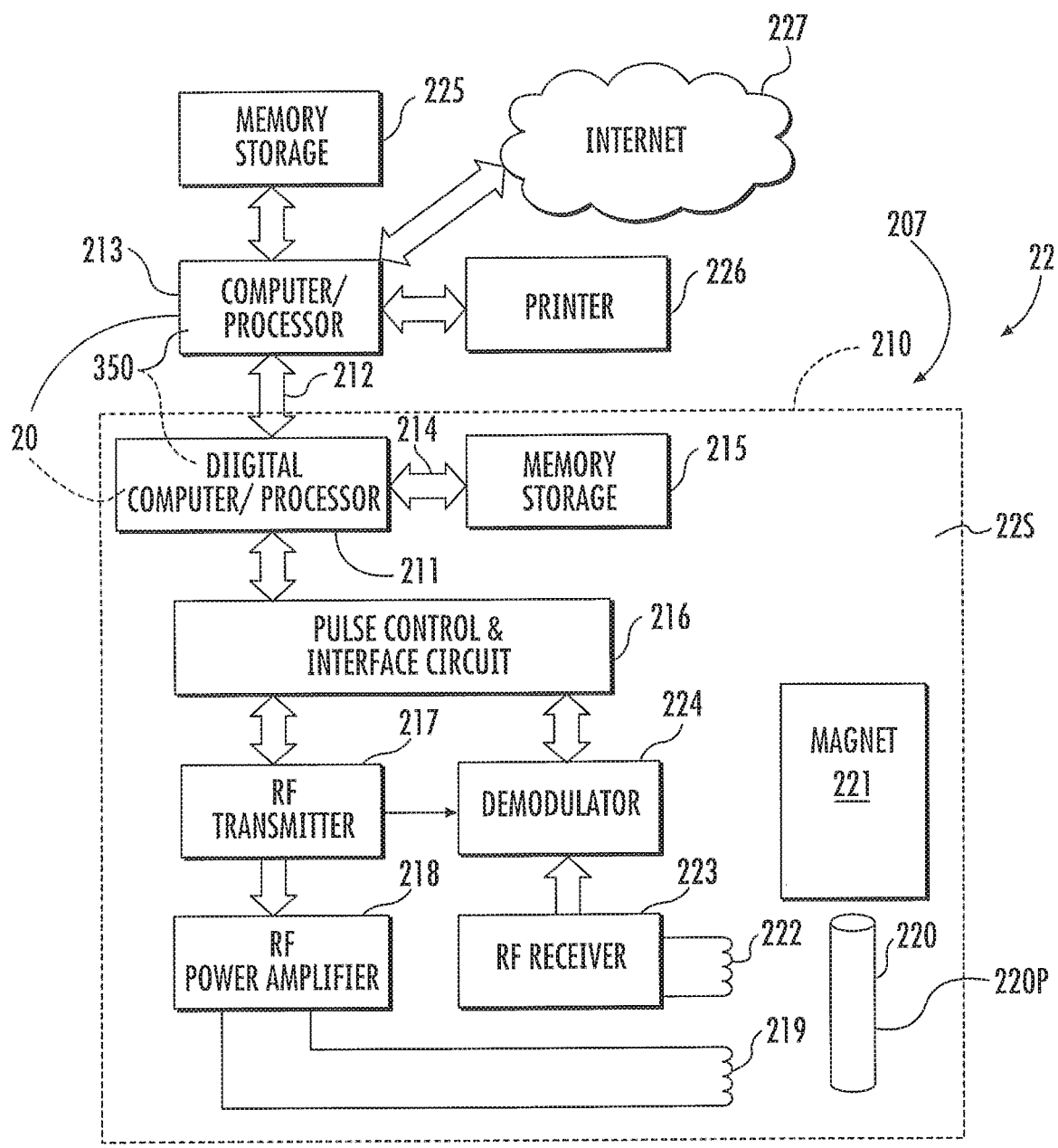
FIG. 18 is a schematic illustration of a NMR spectroscopy apparatus according to embodiments of the present invention.

Referring now to FIG. 18, a system 207 for acquiring and calculating the lineshape of a selected sample is illustrated. The system 207 includes an NMR spectrometer 22s for taking NMR measurements of a sample. In one embodiment, the spectrometer 22s is configured so that the NMR measurements are conducted at 400 MHz for proton signals; in other embodiments the measurements may be carried out at between 200 MHz to about 900 MHz or other suitable frequency. Other frequencies corresponding to a desired operational magnetic field strength may also be employed. Typically, a proton flow probe is installed, as is a temperature controller to maintain the sample temperature at 47+/−0.5 degrees C. The spectrometer 22 is controlled by a digital computer 214 or other signal processing unit. The computer 211 should be capable of performing rapid Fourier transformations. It may also include a data link 212 to another processor or computer 213, and a direct-memory-access channel 214 which can connects to a hard memory storage unit 215.

The digital computer 211 may also include a set of analog-to-digital converters, digital-to-analog converters and slow device I/O ports which connect through a pulse control and interface circuit 216 to the operating elements of the spectrometer 22s. These elements include an RF transmitter 217 which produces an RF excitation pulse of the duration, frequency and magnitude directed by at least one digital signal processor that can be onboard or in communication with the digital computer 211, and an RF power amplifier 218 which amplifies the pulse and couples it to the RE transmit coil 219 that surrounds sample cell 220 and/or flow probe 220p. The NMR signal produced by the excited sample in the presence of a 9.4 Tesla polarizing magnetic field produced by superconducting magnet 221 is received by a coil 222 and applied to an RF receiver 223. The amplified and filtered NMR signal is demodulated at 224 and the resulting quadrature signals are applied to the interface circuit 216 where they are digitized and input through the digital computer 211. The lipoprotein measurement and/or GlycA analyzer circuit 20 and/or module 350 (FIGS. 18-19) can be located in one or more processors associated with the digital computer 211 and/or in a secondary computer 213 or other computers that may be on-site or remote, accessible via a worldwide network such as the Internet 227.

After the NMR data are acquired from the sample in the measurement cell 220, processing by the computer 211 produces another file that can, as desired, be stored in the storage 215. This second file is a digital representation of the chemical shift spectrum and it is subsequently read out to the computer 213 for storage in its storage 225 or a database associated with one or more servers. Under the direction of a program stored in its memory or accessible by the computer 213, the computer 213, which may be a laptop computer, desktop computer, workstation computer, electronic notepad, electronic tablet, smartphone or other device with at least one processor or other computer, processes the chemical shift spectrum in accordance with the teachings of the present invention to generate a report which may be output to a printer 226 or electronically stored and relayed to a desired email address or URI Those skilled in this art will recognize that other output devices, such as a computer display screen, electronic notepad, smartphone and the like, may also be employed for the display of results.

It should be apparent to those skilled in the art that the functions performed by the computer 213 and its separate storage 225 may also be incorporated into the functions performed by the spectrometer's digital computer 211. In such case, the printer 226 may be connected directly to the digital computer 211. Other interfaces and output devices may also be employed, as are well-known to those skilled in this art.

Certain embodiments of the present invention are directed at providing methods, systems and/or computer program products that use GlycA evaluations that may be particularly useful in automated screening tests of clinical disease states and/or risk assessment evaluations for screening of in vitro biosamples.

Embodiments of the present invention may take the form of an entirely software embodiment or an embodiment combining software and hardware aspects, all generally referred to herein as a "circuit" or "module."

As will be appreciated by one of skill in the art, the present invention may be embodied as an apparatus, a method, data or signal processing system, or computer program product. Accordingly, the present invention may take the form of an entirely software embodiment, or an embodiment combining software and hardware aspects. Furthermore, certain embodiments of the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, but is not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium, upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as java7, Smalltalk, Python, Labview, C++, or VisualBasic. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks might occur out of the order noted in the figures. For example, two blocks shown in succession may in fact be executed substantially concurrently or the blocks may sometimes be executed in the reverse order, depending upon the functionality involved.

Figure 19:
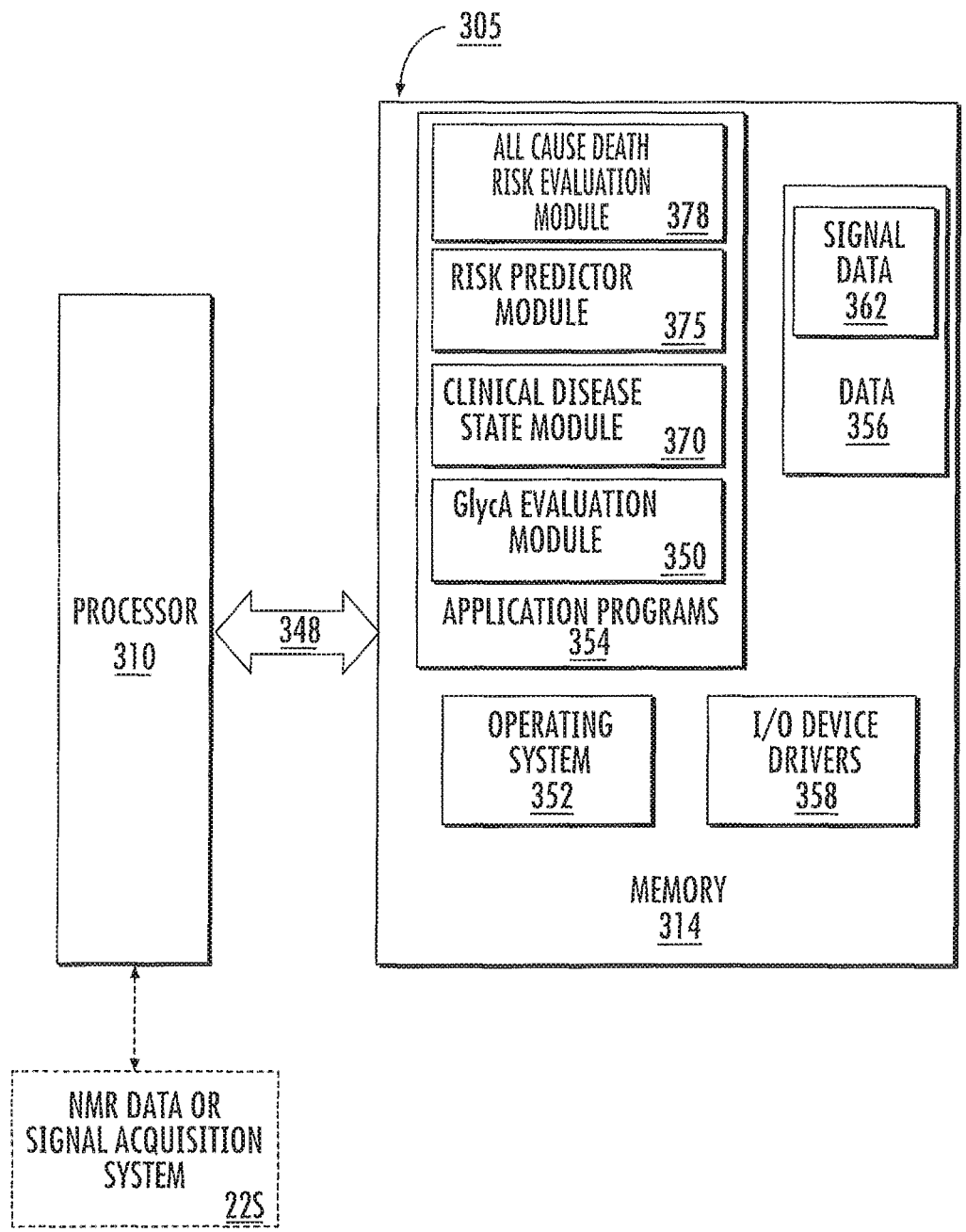
FIG. 19 is a schematic diagram of a data processing system according to embodiments of the present invention.

FIG. 19 is a block diagram of exemplary embodiments of data processing systems 305 that illustrates systems, methods, and computer program products in accordance with embodiments of the present invention. The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM.

As shown in FIG. 19, the memory, 314 may include several categories of software and data used in the data processing system 305: the operating system 352; the application programs 354; the input/output (I/O) device drivers 358; a GlycA Evaluation Module 350; and the data 356. The GlycA Evaluation Module 350 can deconvolve NMR signal to reveal a defined NMR signal peak region in proton NMR spectra of a respective biosample to identify a level of GlycA. The system 305 may also include one or more of a Clinical Disease State Evaluation Module 370 or a Risk Prediction Module 375 that considers the level of the measured GlycA or generates a composite risk number or multi-parameter risk model. The system 305 may also or alternatively include an All Cause Death (ACD) Risk Evaluation Module 378. The ACD Module can programmatically calculate at least one ratio using GlycA in the denominator.

The data 356 may include signal (constituent and/or composite spectrum lineshape) data 362 which may be obtained from a data or signal acquisition system 320 (e.g., NMR spectrometer 22s and/or analyzer 22). As will be appreciated by those of skill in the art, the operating system 352 may be any operating system suitable for use with a data processing system, such as OS/2, AIX or OS/390 from International Business Machines Corporation, Armonk, N.Y., WindowsCE, WindowsNT, Windows95, Windows98, Windows2000 WindowsXP from Microsoft Corporation, Redmond, Wash., PalmOS from Palm, Inc., MacOS from Apple Computer, UNIX, FreeBSD, or Linux, proprietary operating systems or dedicated operating systems, for example, for embedded data processing systems.

The I/O device drivers 358 typically include software routines accessed through the operating system 352 by the application programs 354 to communicate with devices such as I/O data port(s), data storage 356 and certain memory 314 components and/the image acquisition system 320. The application programs 354 are illustrative of the programs that implement the various features of the data processing system 305 and can include at least one application, which supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the Module 350 being an application program in FIG. 19, as will be appreciated by those of skill in the art, other configurations may also be utilized while still benefiting from the teachings of the present invention. For example, the GiycA Module 350, and, where used, one or more of the Clinical Disease State Evaluation Module 370, the Risk Predictor Module 375 or the ACD Risk Evaluation Module 378 may also be incorporated into the operating system 352, the I/O device drivers 358 or other such logical division of the data processing system 305. Thus, the present invention should not be construed as limited to the configuration of FIG. 19, which is intended to encompass any configuration capable of carrying out the operations described herein.

In certain embodiments, the Module 350 includes computer program code for providing a level of GlycA which may be used as an inflammation marker to assess a clinical disease state or risk and/or to indicate whether therapy intervention is desired and/or track efficacy of a therapy or even an unintended consequence of a therapy.

Figure 20:
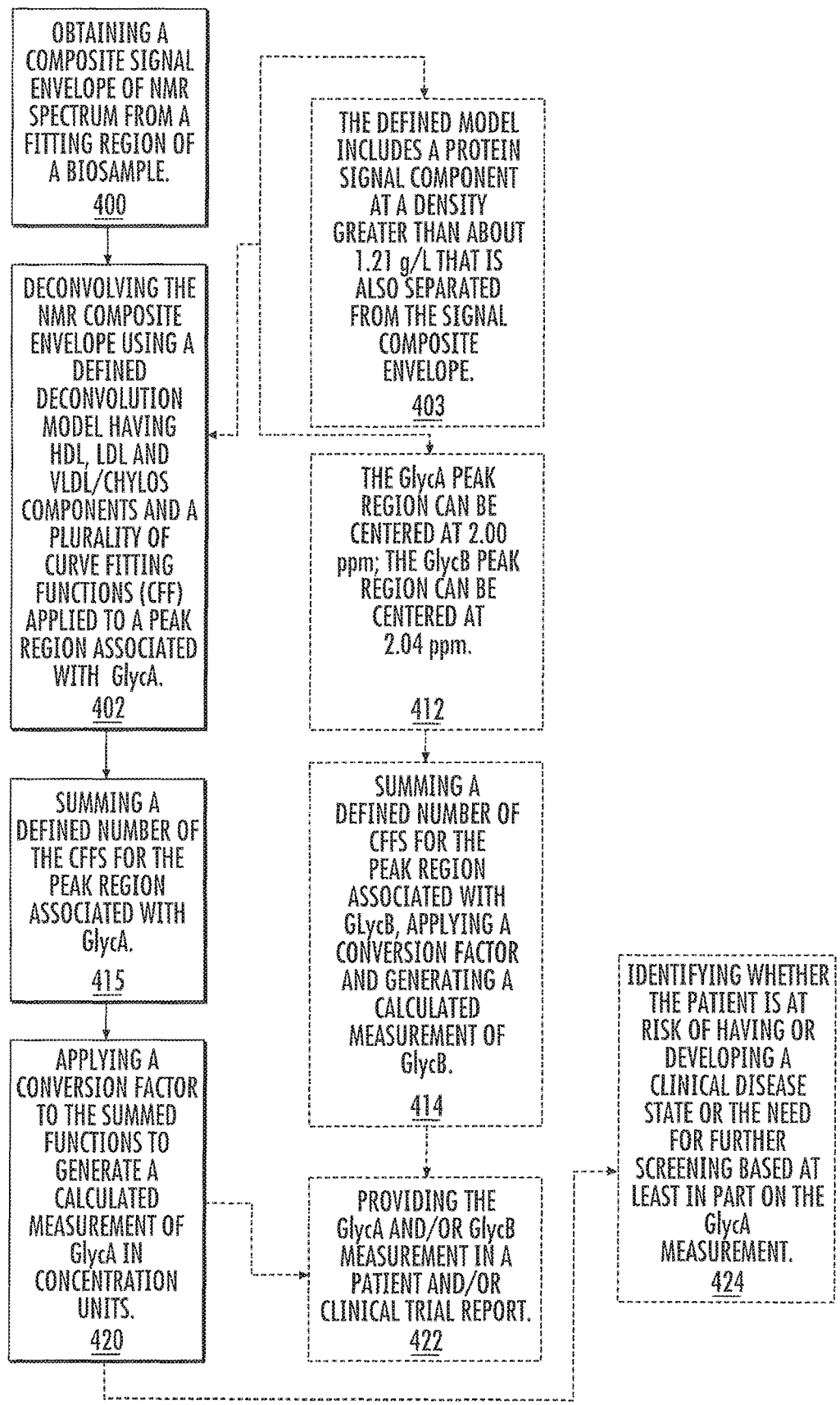
FIG. 20 is a flow chart of exemplary operations that can be used to calculate NMR measures of GlycA according to embodiments of the present invention.

FIG. 20 is a flow chart of exemplary operations that can carry out embodiments of the present invention. A (measured) composite envelope NMR spectrum of NMR spectra of a fitting region of a biosample (e.g., blood plasma or serum) can be obtained (block 400). The NMR composite signal envelope is electronically deconvolved using a defined model having HDL, LDL, and VLDL/Chylos components and a plurality of curve fit (e.g., Lorentzian) functions associated with at least a GlycA peak region centered at a defined chemical shift location (e.g., 2.00 ppm) associated with GlycA (block 402). A defined number of (e.g., Lorentzian and/or Gaussian) curve fit functions for the peak region associated with GlycA can be summed (block 415). A conversion factor can be applied to the summed functions to generate a calculated measurement of GlycA (block 420).

The GlycA and/or GlycB measurement can be provided in a patient and/or clinical trial report (block 422). The report can identify or alert as to whether he or she is at risk of having or developing a clinical disease state and/or whether additional screening may be appropriate, based at least in part on the GlycA measurement (block 424).

The defined model can include a protein signal component at a density greater than about 1.21 g/L, typically above 1.21 g/L, that can be deconvolved/separated from the signal composite envelope (block 403).

The subset of the fitting region can include or extend through a peak region centered at 2.04 ppm for GlycB (block 412). A defined number of (e.g. Lorentzian and/or Gaussian) curve fit functions for the peak region associated with GlycB can be summed and the conversion factor can be applied to generate a calculated measurement of GiycB (block 414).

Figure 21A:
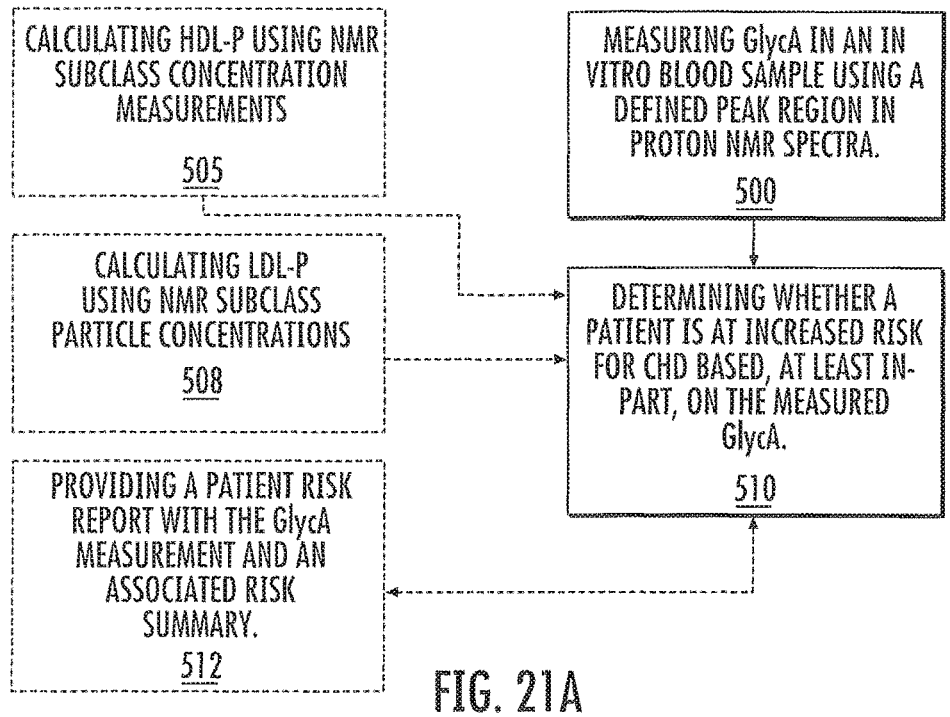
FIG. 21A is a flow chart of exemplary operations that can be used to asses a clinical disease state including, by way of example only, CHD risk, according to embodiments of the present invention.

FIG. 21A is a flow chart of exemplary operations that can carry out embodiments of the present invention. GlycA in an in vitro biosample can be measured using a defined peak region in proton NMR spectra (block 500). A patient's risk of CHD can be determined, at least in part, based on the GlycA measurement (block 510).

The risk can be based on an a priori correlation of the measurement relative to a population norm or standard. The GlycA value and risk association may have a substantially continuous relationship. The increased risk can be associated with an NMR measured GlycA value above a defined population norm. It is contemplated that the risk value or range of values may be associated with values in quartiles 3 and 4, in tertile 3 or above or in quartile 4 or above, as defined by a Hazard Ratio.

The methods may also include calculating HDL-P (block 505) and LDL-P (block 508) using NMR subclass measurements. These parameters can also be evaluated for determining the patient's CHD risk.

The methods may include electronically providing a patient risk report with the GlycA measurement and an associated CHD risk summary (block 512). The risk summary can provide a relative comparison to defined population norms.

Figure 21B:
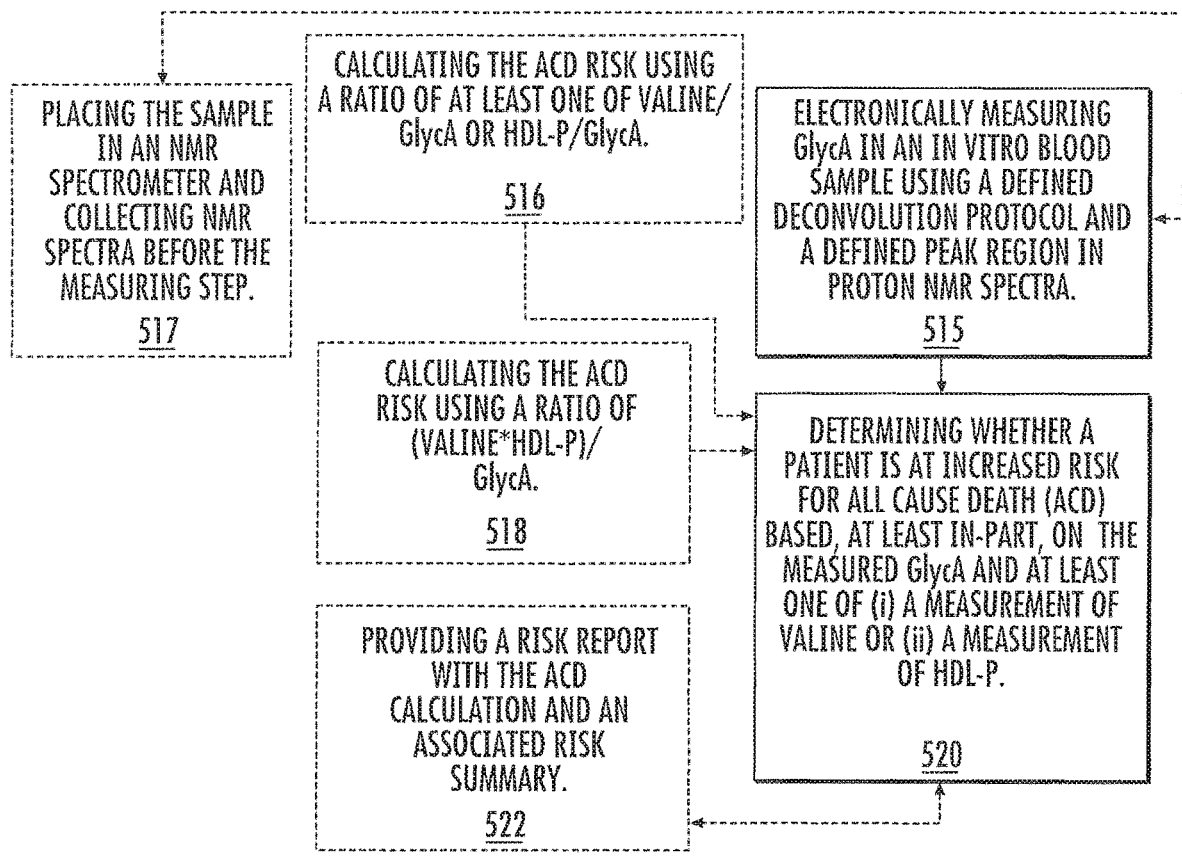
FIG. 21B is a flow chart of exemplary operations that can be used to asses a risk of all-cause death according to embodiments of the present invention.

FIG. 21B is a flow chart of exemplary operations that can be used to carry out other embodiments of the present invention. As shown, GlycA in an in vitro blood sample is electronically measured using a using a defined deconvolution protocol and a defined peak in proton NMR spectra (block 515). The method then determines whether a patient is at increased risk for all cause death (ACD) based on the measured GlycA and at least one of (i) a measurement of valine or (ii) a measurement of HDL-P (block 520). The measurements for the ACD evaluation can be obtained using NMR signal of the same sample.

The determination can be based on a calculation of ACD risk using a ratio of valine/GlycA and/or HDL-P/GlycA (box 516).

The determination can be based on a calculation of ADC risk using a ratio of (valine*HDL-P)/GlycA (block 518). The method may include placing the sample in an NMR spectrometer and collecting NMR spectra before the measuring step (block 517).

The method may include providing a risk report with the ACD measurement and an associated risk summary (block 522). The risk can be based on an a priori correlation of the measurement relative to a population norm or standard (e.g., MESA data or another defined study population). Increased risk of ACD can be associated with a ratio that is below a defined population norm. It is contemplated that the risk value or range of values may be associated with values in Q1 of the ratio (with a highest risk associated with a Q4 or Q5 value of GlycA and a Q1 value of valine or HDL-P and/or Q1 of (valine*HDL-P) as defined by a Hazard Ratio.

Figure 22A:
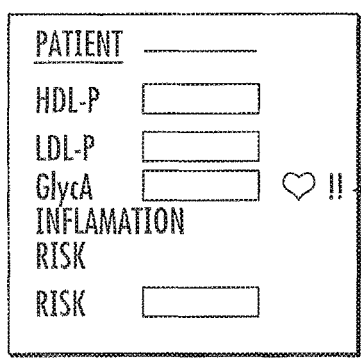
FIG. 22A is an example of a patient report that includes a GlycA measurement according to embodiments of the present invention.
Figure 22B:
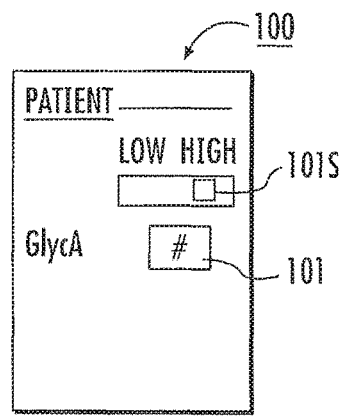
FIG. 22B is an example of a patient report with the GlycA measurement and a closely spaced corresponding risk summary according to embodiments of the present invention.
Figure 22C:
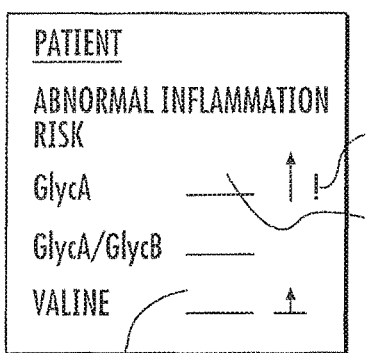
FIGS. 22C-22E are further examples of patient reports according to embodiments of the present invention.

FIG. 22A is a schematic illustration of an exemplary patient test report 100 that can include various lipoprotein parameters such as one or more of Valine, HDL-P, LDL-P, VLDL, and GlycA 101. The GlycA number 101 can be presented with risk assessment summary 101s correlated to population norms, typical ranges, and/or degree of risk (e.g., high, increased or low risk), shown as a sliding scale graph in FIG. 22B. FIG. 22C is an example of a report 100 with a report that includes the NMR measured GlycA value 101 with a risk summary 101s, and one or both of a GlycA/GlycB ratio value 102, and an NMR measure of Valine 103. Ratios or other combinations of these and other analytes or parameters can be provided.

Figure 22D:
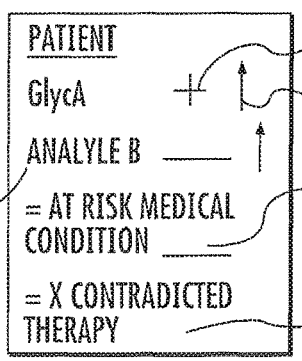

FIG. 22D is an example of a report 100 with the NMR, measured GlycA 101, risk summary 101s, and either (i) at least one other defined NMR measured analyte 101a with a visual notified at-risk indication 101v (either visual indicia of follow-up screening needed or a likelihood of a clinical disease state) or (ii) a notification of a contradicted therapy so as to alert a patient/clinician to avoid certain drug therapies.

Figure 22E:
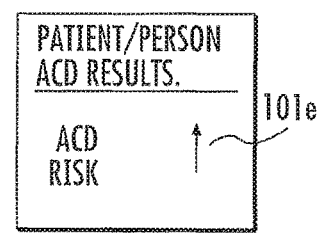

FIG. 22E is an example of a report 100 with a calculated ACD risk 101e indicating a person at elevated ACD risk relative to a population norm.

However, other risk summary configurations may be used including ranges, high to low or low to high, or just noting whether the associated risk is low, medium or increased and/or high.

Figure 23A:
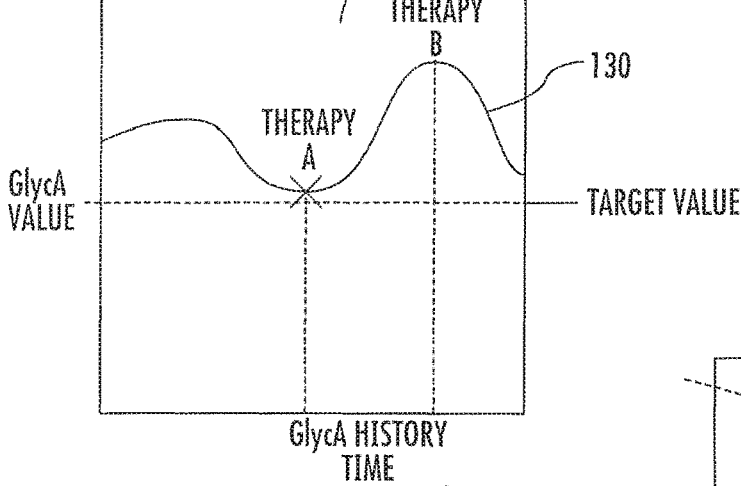
FIG. 23A is a prophetic example of a graph of GlycA versus time that can monitor change to evaluate a patient's risk status and/or one or more clinical disease states, change in status, and/or clinical efficacy of a therapy or even used for clinical trials or to contradict planned therapies and the like according to embodiments of the present invention.

FIG. 23A illustrates that a graph 130 of GlycA values over time can be provided to illustrate a change in patient health and/or inflammatory status over time due to age, medical intervention or a therapy according to some embodiments. Tracking this parameter may provide a clinical indicator of efficacy of a therapy and/or a better risk predictor for CHD other clinical disease states or all-cause death risk, for patients.

As shown in FIG. 23A, the analysis can be used to monitor a patient over time to correlate known start or use of a drug or other therapy. Future drugs or uses of known drugs can be identified, screened or tested in patients identified using GlycA evaluations.

Figure 23B:
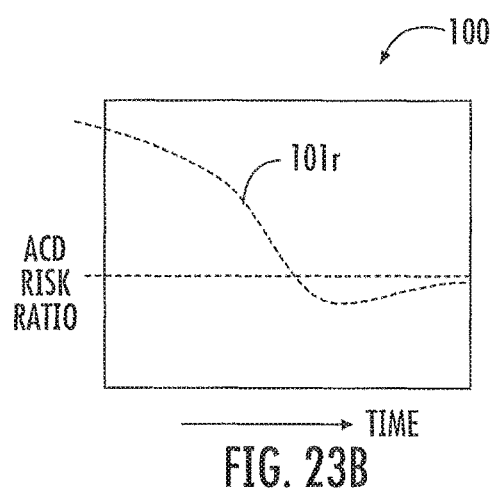
FIG. 23B illustrates a prophetic example of a graph of a calculated ACD risk ratio over time that can be monitored to assess health status or a change of health status (or a change in risk according to embodiments of the present invention.

FIG. 23B illustrates a graph of a calculated ACD risk ratio 101r using GlycA in the denominator can be monitored over time similarly to the GlycA alone. It is contemplated that both values may also be monitored for changes over time reflective of a therapy or change in health status and/or to evaluate a patient's risk status and/or change in status, clinical efficacy of a therapy or even used for clinical trials or to contradict planned therapies.

FIG. 24 is a table showing prediction of all-cause death in MESA (n=5712). The prediction of all-cause death (n=346) for various parameters and combinations of parameters is from logistic regression analyses adjusted for age, gender, race, smoking, systolic blood pressure, hypertension medications, body mass index, diabetes, and LDL-P. The model likelihood ratio $\chi^2$ statistic provides a quantitative measure of the risk prediction given by that model, allowing comparisons of how much each parameter improves prediction of incident death when added to the 9 covariates in the regression model. As shown, HDL-P, GlycA and valine are all strong predictors of ACD and each is independent of the other. Thus, alone each is better than the conventional TC/HDL-C ratio and combined these factors can provide an even more effective way to stratify people in terms of their ACD risk.

Figure 25A:
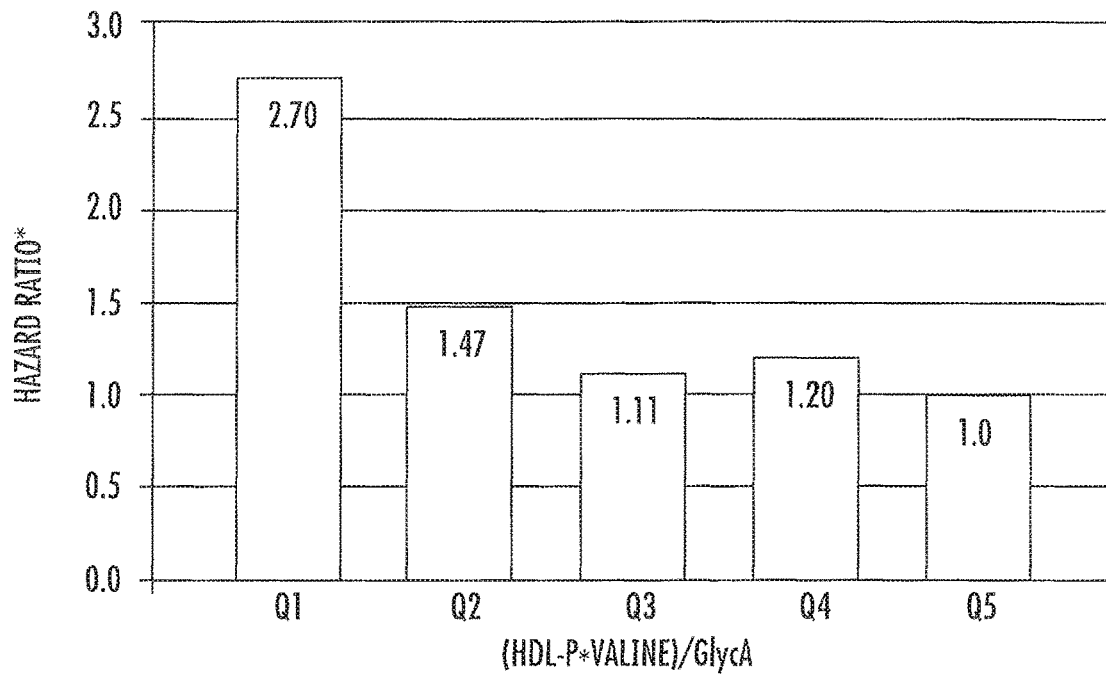
FIG. 25A is a graph of Hazard Ratio versus quintile of (HDL, P*Valine/GlycA) according to some embodiments of the present invention.

FIG. 25A illustrates how risk of death differs as a function of the calculated risk predictor in quintiles of (HDL-P*Valine)/GlycA. FIG. 25A is a graph of Hazard Ratio for all-cause death (n=346) from Cox proportional hazards regression analyses adjusted for age, gender, and smoking. The risk for values in the first quintile (Q1) are almost double (about 1.8×) that in the second quintile (Q2).

Figure 25B:
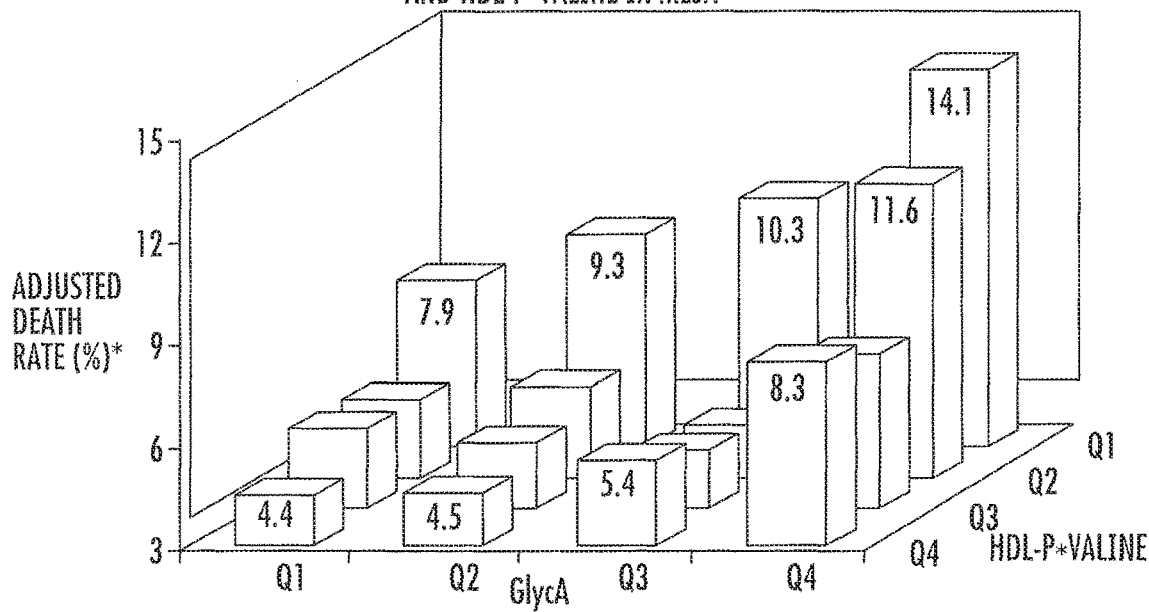
FIG. 25B is a three dimensional graph of adjusted death rate for GlycA and (HDL-P*Valine) in quartiles for each parameter according to embodiments of the present invention.

FIG. 25B is a three-dimensional graph (16 subgroups) of adjusted death rate (%) as a function of GlycA quartiles (x-axis) and HDL-P*Valine quartiles (y-axis). The lowest death rate (4.4%) is seen for those with low GlycA (Q1) and high HDL-P*Valine (Q4), whereas the highest death rate (14.1%) is observed for those with high GlycA (Q4) and low HDL-P*Valine (Q1). The death rate (%) is based on a 7-year follow-up period, adjusted for age, gender and smoking.

Figure 26A:
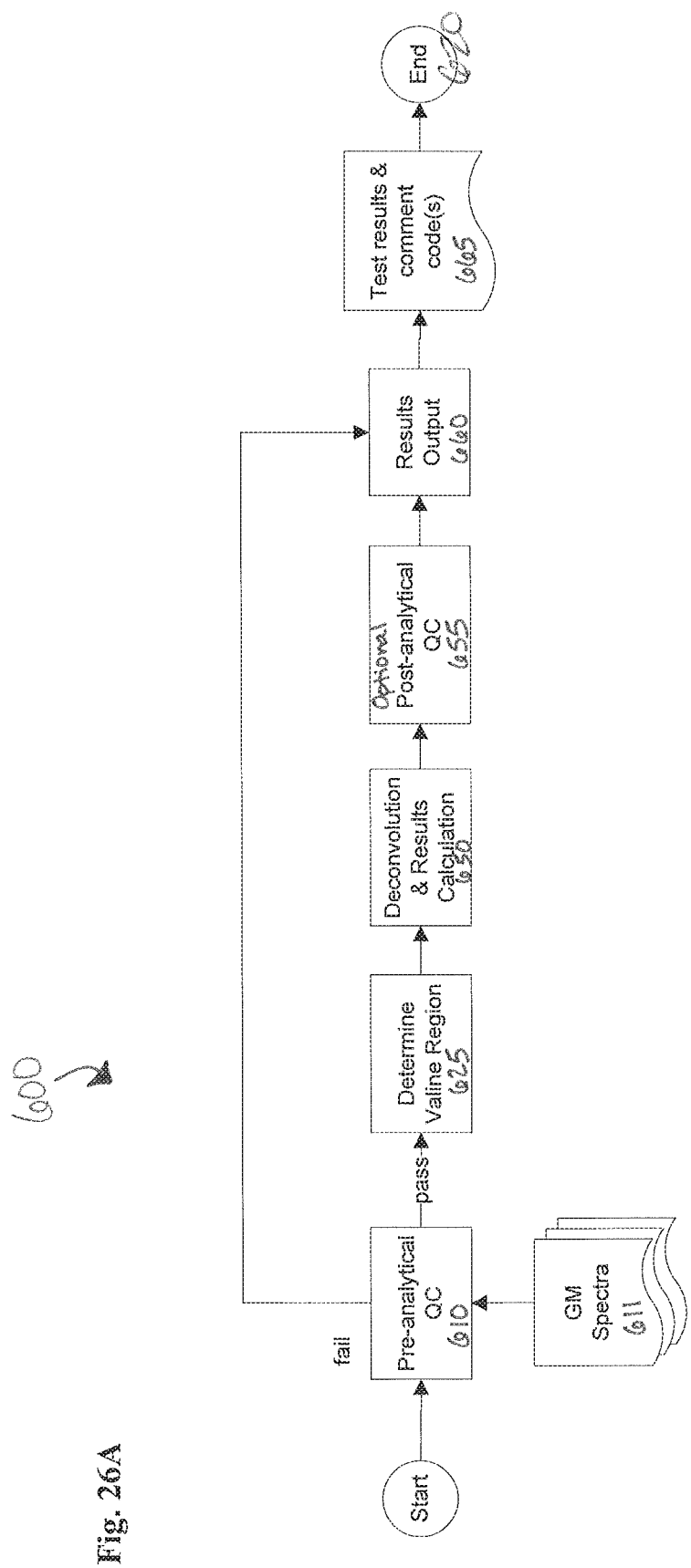
FIG. 26A is a flow diagram of an NMR valine test protocol according to embodiments of the present invention.
Figure 26B:
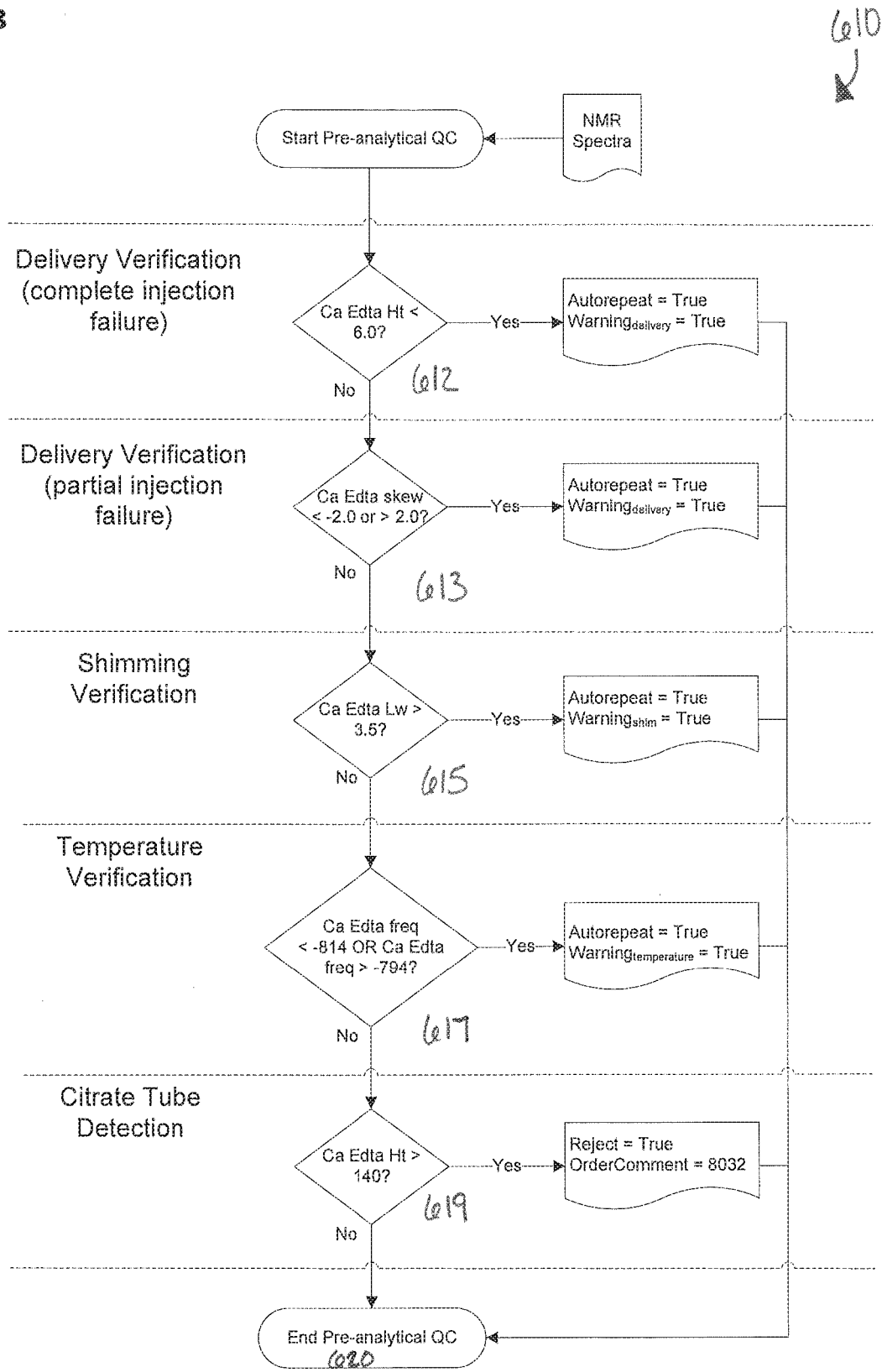
FIG. 26B is a flow chart of exemplary pre-analytical processing that can be used prior to obtaining NMR signal of biosamples according to embodiments of the present invention.
Figure 26C:
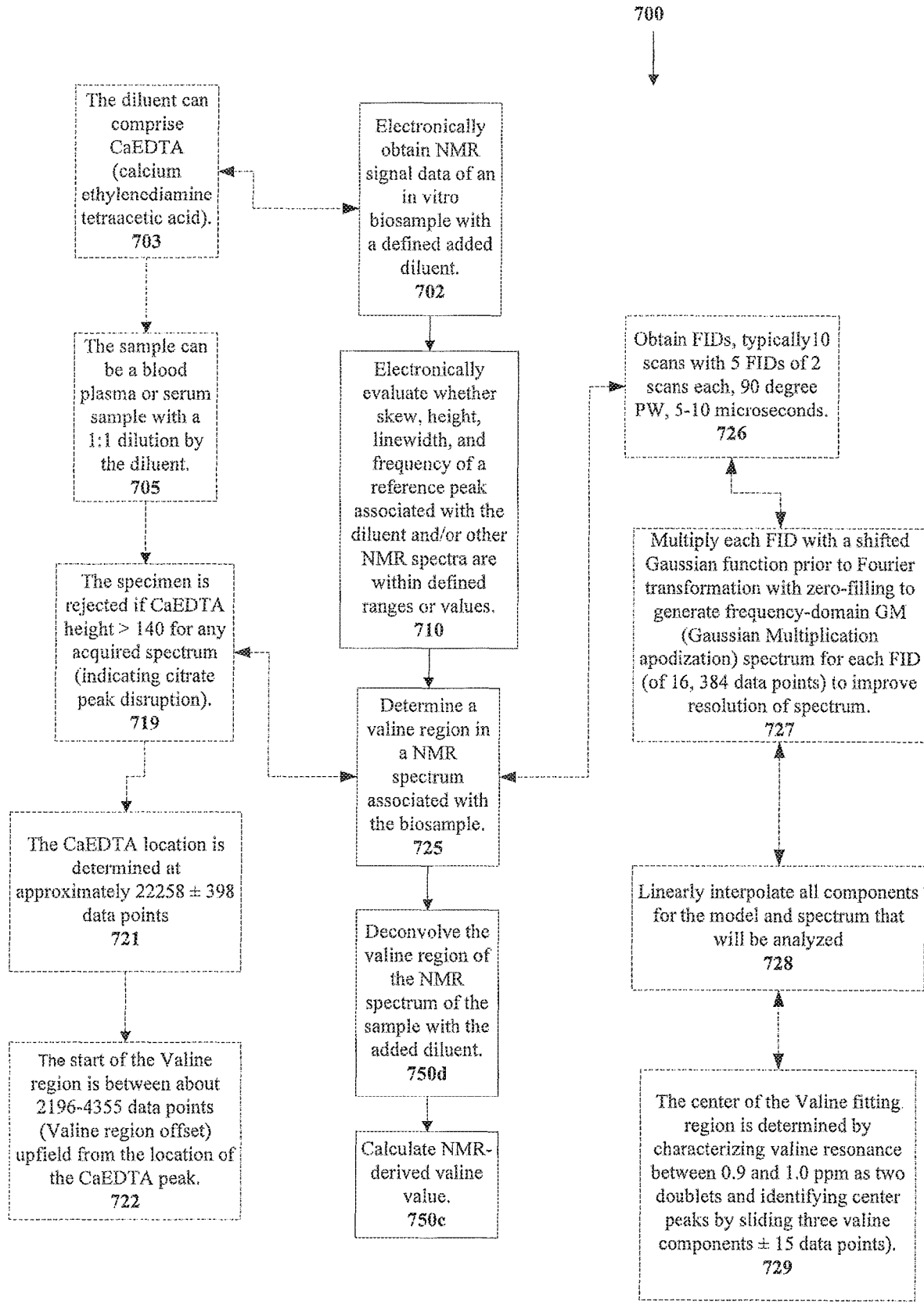
FIG. 26C is a flow diagram of operations that can be used to evaluate valine using NMR according to embodiments of the present invention. The foregoing and other objects and aspects of the present invention are explained in detail in the specification set forth below.

FIGS. 26A-26C are exemplary flow diagrams of operations that can be used to obtain NMR signal associated with valine according to embodiments of the present invention.

FIG. 26A illustrates that a pre-analytical evaluation (block 610) can occur before a valine region of the NMR signal is determined (block 625), then deconvolved (block 650). FIG. 26B illustrates an exemplary pre-analytical evaluation 610 which includes delivery verification of the sample into the flow cell as either complete failure (block 612) or partial injection failure (block 613), shimming verification (block 615), temperature verification (block 617) and a citrate tube detection (failure) (block 619), all using defined characteristics of signal associated with a defined diluent added to the sample.

Referring again to FIG. 26A, once the defined parameters are confirmed within the pre-analytical quality control analysis can end (block 620) and the determination of the valine region can be identified (block 625) and the spectrum deconvolved and valine level calculated (block 650). Optionally, a post-analytical quality control can be electronically performed (block 655) and the results output (block 660). The results can be included in a test report with comments, visual indicia of high or low and the like (block 665).

Referring to FIG. 26C, a method/analysis 700 of operations that can be used to quantify valine are shown. NMR signal can be electronically obtained of an in vitro biosample with a defined added diluent (block 702). The QC evaluation can be carried out (block 710). The valine region is determined (block 725). The valine region is deconvolved (block 750d) and an NMR derived value of valine is calculated (750c).

The diluents can comprise calcium ethylenediamine tetraacetic acid (Ca EDta) (block 703) or other suitable diluent that creates a reliable peak and behaves in a predictable manner. Well established chemical shift or quantitation references include, for example, formate, trimethylsilylpropionate (and isotopically labeled isomers), and EDTA.

The pre-analytical quality control evaluation 710 can be based on inspection of characteristics of the CaEDTA reference peak and the system or processor can be configured not to perform the Valine test unless the NMR spectra have been acquired under specified conditions such as those shown in FIG. 26B. The sample temperature can be 47±0.5° C. in the flow cell for NMR scans/signal acquisition. The sample can comprise diluents in a 1:1 ratio (block 705) or other defined ratio (e.g., more sample, less diluents or more diluent; less sample, e.g., 2:1 or more sample, less diluents, e.g. 1:2).

The test sample can be rejected with a defined error code if CaEDTA height>140 for any acquired spectrum (block 719). This high value is indicative of detection of the citrate peak in conjunction with the CaEDTA peak. The citrate peak is introduced by collection of the specimen in an improper citrate tube. By disrupting the ability to locate the exact position of the CaEDTA peak, the citrate peak can disrupt the process for determining the Valine region.

The Valine region is located upfield relative to the position of the CaEDTA peak. The broad peaks beneath Valine are various methyl (—CH$_3$—) protons of lipoproteins. The CaEDTA location can be determined at approximately 22258±398 data points (block 721). The Valine region can be determined independently for each acquired spectrum. The Valine signal can be modeled with suitable data points using, for example, 25 data points (center±12 data points) for each peak of the quartet or 300 data points for the valine region of both doublets, but other numbers of data points may be used. The measurement of Valine can be carried out using one, two, three or all four peaks of the valine peak quartet.

All basis set spectra can be linearly interpolated before utilized by the non-negative least squares algorithm. The spectra to be analyzed and the basis set spectra can have a zero baseline offset modification before utilized by the non-negative least squares algorithm.

The start of the Valine region can be at about 2196-4355 data points, typically the latter when including both doublets, (the "Valine region offset") upfield from the location of the CaEDTA peak (block 722). In some embodiments, the start of the valine region is at 4355 datapoints upfield from the location of the CaEDTA peak.

In some embodiments, the valine quantification is carried out by characterizing the valine resonances at between 0.0-1.01 ppm as two doublets. Three or more valine experimental spectra stepped by two data points can be used as basis sets to model valine signal. The center valine peaks can be located by sliding three valine components +/−15 data points and determined through a least squares sum minimization. The valine signal can be modeled with a total of about 300 data points.

Each basis set, including those used for the baseline but excluding the DC offset, are offset such that the lowest value is subtracted from the function (making the lowest point equal to 0). This prevents inclusion of a DC offset in the shapes they represent.

The Valine region from each acquired spectrum is deconvolved with a series of analyte and baseline functions which have been treated to the same type of pre-processing as the acquired spectra. The deconvolution coefficient for each component can be multiplied by an associated conversion factor. The current Valine embodiment has a conversion factor of 2271 to report Valine in μM units; however, this value can vary by ±10% without unduly affecting the reported value significantly.

| Component Name | Filename | Conversion Factor | Basis Function Starting position relative to CaEDTA |
|---|---|---|---|
| Valine1 | Valine318LB019.1r | 2271 | −4353 |
| Valine2 | Valine318LB019.1r | 2271 | −4355 |
| Valine3 | Valine318LB019.1r | 2271 | −4357 |

The resulting values are summed. Result values produced independently for each acquired spectrum can be averaged to generate final values to use in the measurement.

Data can be acquired using presaturation water suppression from a 1:1 diluted sample and can include between 5-20 scans, typically about 1.0 scans stored as 5 blocks of 2 (5 FIDs consisting of 2 scans each) (block 726).

The pulse sequence used in conjunction with presaturation water suppression can optionally include a presaturation (water suppression) pulse and a suitable excitation pulse. FIDs can be acquired with 9024 data points with a sweep width of 4496.4 Hz. Each FID can be multiplied with a shifted Gaussian function:

$$e^{-\left(\frac{(t-gfs)}{gf}\right)^2},$$

or in computer terms, exp(−((t−gfs)/gf)^2), where gfs=0.2 seconds and gf=0.2 seconds.

This can be performed prior to Fourier transformation with zero-filling which yields the frequency-domain GM spectrum for each FID consisting of 16,384 data points (block 627). The spectra can be phased using the calibration-specified phase value. The spectra can be sealed (multiplied) by a calibration-specified scaling factor. All basis set spectra can be linearly interpolated before utilized by the non-negative least squares algorithm. The spectra to be analyzed and the basis set spectra can have a zero baseline offset modification before utilized by the non-negative least squares algorithm (e.g., all components used for the model and the spectrum that will be analyzed can be linearly interpolated) (block 728). To determine the center of the valine fitting region, the valine resonances between 0.9 and 1.0 as two doublets can be characterized and the center peaks can be identified by sliding three valine components ±15 data points (block 729).

Examples of Uses of GlycA and/or GlycB along or with other parameters and/or analytes
    All-Cause Death (ACD) Risk Prediction
    ACD Risk Ratios
    CHD Risk Evaluation
    Diabetes Evaluation
    CHD Risk Evaluation using GlycA and HDL-P and/or LDL-P
    Mass Screening for At-Risk Medical Condition. The NMR GlycA measurement can be a standardized test parameter that can be generated from a blood plasma sample being analyzed for other test parameters including for example, magnesium, valine, lipoprotein particles such as HDL-P or LDL-P and the like.
    Identification of a likelihood that the patient has or is at risks of having a Clinical Disease State.
    Evaluating Drug Therapy for intended or unintended reactions and/or contradictions.
    Evaluating Patient Response in Clinical Trials.
    Evaluating Animal Response in Drug Development/Screening.
    Use of GlycA/GlycB Ratio to identify risk or a clinical disease state.
    Use of GlycA with one or more Secondary Analytes including HDL-P, LDL-P, Mg or Valine to identify risk or a clinical disease state.
    Generating a risk predictor index using HDL-P/LDL-P*GlycA for CHD risk.
    Monitoring Inflammation Status of a Patient over Time to indicate when medical intervention may be appropriate (additional screening or therapy).
    Evaluating risk of developing or whether a person has Dementia using GlycA. The Dementia evaluation can use both GlycA and valine measurements as separate components and/or as a ratio.
    Evaluating a patient's risk of stroke based on the measured level of GlycA and Mg.
    Evaluating risk of colorectal cancer using GlycB.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of measuring GlycA, an NMR biomarker derived from a measure of composite NMR signal from carbohydrate portions of acute phase reactant glycoproteins containing N-acetylglucosamine and/or N-acetylgalactosamine moieties, comprising:
performing Nuclear Magnetic Resonance to obtain a composite NMR spectrum of a fitting region of a biosample of a subject, wherein the spectrum is acquired using a one-pulse sequence;
deconvolving the composite NMR spectrum using a defined deconvolution model with high density lipoprotein (HDL) components, low density lipoprotein (LDL) components, VLDL (very low density lipoprotein)/chylomicron components, and a plurality of curve fit functions associated with at least a GlycA peak region from 1.845 ppm to 2.080 ppm; and
generating a measure of GlycA using the curve fit functions.

2. The method of claim 1, further comprising applying a conversion factor to the measure of GlycA to provide the measure in μmol/L.

3. The method of claim 1, wherein the curve fit functions are overlapping Lorentzian functions, and wherein the measure of GlycA is generated by summing a defined number of Lorentzian functions.

4. The method of claim 1, wherein the deconvolution model further comprises a protein signal component for protein having a density greater than 1.21 g/L.

5. The method of claim 2, wherein the deconvolution model further comprises a protein signal component for protein having a density greater than 1.21 g/L, and wherein the method further comprises generating a risk predictor using a mathematical equation of: HDL-P/LDL-P*GlycA, wherein HDL-P is an NMR measure of HDL particle number and LDL-P is an NMR measure of LDL particle number and GlycA in the equation is the GlycA measurement, all in μmol/L.

6. The method of claim 1, further comprising deconvolving another part of the NMR spectrum of the sample associated with a quartet of valine signals and generating an NMR measure of valine.

7. The method of claim 5, further comprising providing the valine and GlycA measurement in a test report.

8. The method of claim 1, wherein the plurality of curve fit functions are overlapping Lorentzian functions.

9. The method of claim 1, wherein the biosample comprises blood plasma or serum, wherein the obtaining comprises obtaining NMR signal of the biosample while the biosample is at 47 degrees C.+/−0.2 degrees in an NMR probe of an NMR spectrometer and wherein the GlycA peak region is centered at 2.00 ppm.

10. The method of claim 1, wherein the plurality of curve fit functions are applied to a fitting region that includes the GlycA peak region with between about 40-50 curve fit functions, and wherein the generating the measure of GlycA is carried out by summing values of a defined first subset of the curve fit functions.

11. A method of determining coronary heart disease (CHD) risk for a patient, comprising:
performing Nuclear Magnetic Resonance on a biosample from a subject to obtain a proton NMR spectrum, wherein the spectrum is acquired using a one-pulse sequence;
evaluating NMR signal in a defined peak region of the proton NMR spectrum associated with GlycA of the biosample to determine a level of GlycA, wherein GlycA is an NMR biomarker derived from a measure of composite NMR signal from carbohydrate portions of acute phase reactant glycoproteins containing N-acetylglucosamine and/or N-acetylgalactosamine moieties;
and determining a patient's risk of CHD based, at least in part, on the level of GlycA, wherein the defined peak region is centered at 2.00 ppm and extends from 1.845 ppm to 2.080 ppm for a sample at 47+/−0.2° C. in an NMR spectrometer.

12. A method to evaluate or predict all-cause death risk of a person, comprising:
measuring GlycA according to claim 1;
calculating a ratio of measurements of at least one of the following: Valine to GlycA, HDL-P to GlycA or (Valine*HDL-P)/GlycA from the NMR spectrum; and
evaluating whether the person has an increased risk for all-cause death relative to a defined population, wherein the person has increased risk relative to the defined population when the calculated ratio is in a first tertile, first quartile or first quintile of the population.

* * * * *